United States Patent [19]
Ryan

[11] Patent Number: 6,115,636
[45] Date of Patent: Sep. 5, 2000

[54] TELEMETRY FOR IMPLANTABLE DEVICES USING THE BODY AS AN ANTENNA

[75] Inventor: Terence G. Ryan, Palm Coast, Fla.

[73] Assignee: Medtronic, Inc., Minneapolis, Minn.

[21] Appl. No.: 09/218,946

[22] Filed: Dec. 22, 1998

[51] Int. Cl.[7] ........................................ A61N 1/37
[52] U.S. Cl. ........................ 607/60; 128/903; 607/32
[58] Field of Search ............................ 128/903; 607/30, 607/32, 60

[56] References Cited

U.S. PATENT DOCUMENTS

| | | | |
|---|---|---|---|
| 4,248,241 | 2/1981 | Tacchi | 128/903 |
| 4,543,955 | 10/1985 | Schroeppel | 607/30 |
| 4,625,733 | 12/1986 | Saynajakangrs | 128/903 |
| 4,987,897 | 1/1991 | Funke | 607/32 |
| 5,562,713 | 10/1996 | Silvian | 607/60 |

*Primary Examiner*—William E. Kamm
*Attorney, Agent, or Firm*—Girma Wolde-Michael; Beth L. McMahon; Harold R. Patton

[57] ABSTRACT

A telemetry system and method includes an implantable medical device implanted in a body and an external communication device, e.g., a programmer. The implanted device includes a housing having transmitter/receiver circuitry positioned therein. The external communication device includes transmitter/receiver circuitry connected to an antenna thereof. The transmitter/receiver circuitry of the implanted device is electrically coupled to the body such that the body functions as an antenna for the implanted device to facilitate communication of data between the implanted device and the external communication device.

65 Claims, 14 Drawing Sheets

TELEMETRY FOR IMPLANTABLE DEVICES USING THE BODY AS AN ANTENNA

FIELD OF THE INVENTION

The present invention relates generally to the field of telemetry. More particularly, the present invention pertains to telemetry for implantable devices which allows for communication between implanted devices and communication devices external to the body.

BACKGROUND OF THE INVENTION

A wide variety of implantable medical devices are known and commercially available. Generally, implantable medical devices typically have a metal case and a connector block mounted to the metal case which includes receptacles for leads. Such leads may be used for electrical stimulation or for sensing of physiological activity or conditions. For example, an implantable cardiac device, e.g., a pacemaker, may use such leads to monitor activity of a human heart and also may additionally be used to perform therapy for the human heart. In other words, for example, heart activity may be monitored using the implantable device by sensing electrical signals generated by the heart, recording data indicative of the sensed electrical signals, and analyzing the recorded data to provide characterization data of the heart activity. Such implantable medical devices, e.g., such as those under the direction of a microprocessor, may generate data indicative of various conditions indicated by such heart activity and store data in memory.

It is generally desired, that data stored in implantable memory devices be provided to a physician or other personnel for collection and/or analysis. Further, due to various factors, such as the complexity of implantable medical devices; the need to diagnose, optimize and adjust various parameters during the implant procedure for such implantable medical devices; the occurrence of physiological changes; implantable device variables or drifts; and the need to retrieve data for analysis from the implantable medical device, extensive telemetry capabilities between implantable medical devices and external devices, e.g., an external programmer, are required. For example, the need to access system performance or trouble-shoot the patient, device, and/or lead system in an acute, clinical setting requires such telemetry capability between the implanted medical device and an external device.

Programmers used to adjust parameters of multi-function implantable medical devices typically include graphic displays, keyboards, or light pens for data entry and device control by operator manipulation, and also include printers or plotters to allow the user to easily control, evaluate, and document the extensive capabilities of the medical device. For example, such devices may include the Medtronic Model 9760 programmer.

Typically, a programmer used during a telemetry procedure is positioned remote from the patient. A programming head of the programmer, e.g., a wand or some other external device, containing at least an antenna, is connected to the remainder of the programmer via a stretchable coil cable and is positioned over the patient's implanted device site for programming or telemetry interrogation of the implanted device. The programmer typically consists of one or more microprocessors and contains programmable memory capable of storing executable programs under the control of the operator via a user interface. The implantable medical device may receive command instructions from the non-implanted external device, e.g., the programmer, which is external to the skin of the patient. Such command instructions are referred to herein as downlink transmissions, i.e., transmissions from the external device or programmer to the implantable medical device. For example, the received command instructions may include program instructions or steps for directing the operation of the implantable medical device. Further, for example, the received command instructions may also include data such as program limits and timing data.

Similarly, the implantable medical device may transmit data to the external device, e.g., programmer. Such transmissions are referred to herein as uplink transmissions, i.e., transmissions from the implantable medical device to the external device. In other words, the programmer may function to receive data from the implantable medical device as well as to transmit the commands thereto. Communication between the implanted device and the external device may be limited to transmissions by only one of the devices with the other device receiving those transmissions. Alternatively, communication between the implanted medical device and the external device may include transmissions by both devices.

The communication between the implanted medical device and the external device, e.g., programmer, is facilitated by receiving and transmitting circuitry included within the implanted medical device and the external device. The implanted medical device includes receiver and transmitter circuitry which may cooperate with other circuitry of the implanted medical device to receive information from the external device and to transmit data to the external device. Further, the external device includes analogous transmitting and receiving circuitry for communicating with the implanted medical device. Both the implanted medical device and the external device include antenna structures coupled to the receiver and transmitter circuitry for transmitting and receiving electromagnetic energy.

Various systems for performing telemetry with regard to implanted devices are known. For example, such systems are described in U.S. Pat. No. 5,127,404 issued to Wyborny, et al.; U.S. Pat. No. 4,556,063 issued to Thompson, et al.; and U.S. Pat. No. 5,342,408 issued to de Coriolis et al. Such conventional telemetry systems typically enclose the antenna or antennas of the implanted medical device inside the housing or case of the implantable device. As described above, such housings are typically metallic in nature and may be, for example, made of titanium or titanium alloys. Such metal housings may act as low pass filters to limit the bandwidth of signals transmitted from and received by the implanted medical devices. Conventional telemetry systems which enclose the antennas in the case generally have undesirably low transmission rates. Further, operation is forced to the lower frequency ranges due to the attenuation of higher frequencies by the case of the implanted device.

In such conventional telemetry systems, bandwidth is kept low to minimize the power consumed by the implanted medical device. Power consumption is a very important criteria in designing implantable medical devices. Such devices are typically powered by a depletable energy source, such as a battery. A depleted energy source requires replacement of the implanted device, which can be costly and is inconvenient.

Accordingly, there is a need to minimize power consumption by the implanted medical device. Various techniques of minimizing power consumption for telemetry functions have been described. For example, minimization of power consumption as described in U.S. Pat. No. 5,342,408 is accomplished by the intermittent use of receiving and transmitting circuitry of the implanted medical device to communicate with the programmer. In other words, transmitter and receiver circuitry are de-energized to reduce power consumption when such circuitry does not need to be activated. As such, there becomes a need to wake up the de-energized portions of the implanted medical device when desired to allow communication to occur. However, generally, a relatively large receiving antenna for the implanted medical device is required to couple sufficient electromagnetic energy to the receiving circuitry thereof to facilitate such a wake up function. Such an antenna is undesirable and inconsistent with a physically compact implanted medical device.

In addition to power reduction, another important design criterion for implanted medical devices is accurate communication of data between the external device and the implanted device. Downlink transmissions from the programmer to the implanted medical device must be received correctly. Similarly, uplink transmissions by the implanted medical device to the external device must be received correctly. This communication must occur in environments such as hospitals and doctors offices, which may be very noisy due to the presence of other electronic and electromagnetic sources. One aspect of assuring accuracy of transmitted data is establishing a reliable data link.

Generally, the external device's antenna is disposed in a moveable programmer head which is to be placed in close proximity to the implantation site of the implanted medical device to effect a reliable data link in conventional telemetry systems. Because the medical device is implanted and not visible, determining the proper orientation of the programming head of the external device can be difficult. To assure that the data is transmitted accurately, programming head antennas must be positioned to maximize signal strength received from the implanted medical device. As described in U.S. Pat. No. 5,342,408, a moveable programming head positioned external to the patient can include a signal strength indicator giving an indication of received signal strength to allow repositioning of the moveable programming head to maximize received signal strength. However, the physician handling the programming head has various tasks to perform and repositioning of the programming head to a particular position and maintaining such a position to maximize received signal strength is a task that makes completing the telemetry functions undesirably difficult.

Various references describe using the human body for communication functions. For example, U.S. Pat. No. 4,987,897 to Funke, entitled, "Body Bus Medical Device Communication System," describes using the human body as the communication transmission channel between two or more implantable modules and/or between at least one implantable module and an external skin electrode intended for connection to an external module. Further, U.S. Pat. No. 5,113,859 to Funke, entitled, "Acoustic Body Bus Medical Device Communication System," describes using the human body for ultrasonic coupling between two or more implantable modules and/or between at least one implantable module and an external skin transducer intended for connection to an external module. U.S. Pat. No. 5,796,827 to Coppersmith, et al., entitled, "System and Method For Near-Field Human-Body Coupling for Encrypted Communication with Identification Cards," describes a communication system wherein transmitter and receiver components of the communication system are capacitively coupled using the human body. Such communication systems using the human body for capacitive coupling are also described in an article entitled, "Personal Area Networks: Near-field intra-body communication," by T. G. Zimmerman, *IBM Systems Journal*, Vol. 35, Nos. 3 & 4 (1996) and in PCT International Publication No. WO 96/36134, entitled, "System For Non-Contact Sensing and Signaling Using Human Body as Signal Transmission Medium."

Further, U.S. Pat. No. 4,440,173 to Hudziak et al., entitled "Programmable Body Stimulation System" describes a stimulation system having a stimulation signal generator located within a housing for implantation in the body such that stimulation signals can be delivered by a lead to a desired body site. The lead used for delivering the stimulation signals is also allegedly used for receiving programming signals and delivering such signals to operating characteristic establishing circuitry of the system. This allegedly eliminates the need for an antenna coil within the housing for receiving such programming signals.

Table 1 below lists U.S. patents relating to communication techniques:

TABLE 1

| U.S. Pat. No. | Inventor(s) | Issue Date |
| --- | --- | --- |
| 5,113,859 | Funke | 19 May 1992 |
| 5,678,202 | Filimon, et al. | 14 October 1997 |
| 4,440,160 | Fischell, et al. | 3 April 1984 |
| 4,471,786 | Inagaki, et al. | 18 September 1984 |
| 4,440,173 | Hudziak, et al. | 3 April 1984 |
| 4,481,950 | Duggan | 13 November 1984 |
| 4,886,064 | Strandberg | 12 December 1989 |
| 4,987,897 | Funke | 29 January 1991 |
| 5,312,446 | Holscabach, et al. | 17 May 1994 |
| 5,796,827 | Coppersmith, et al. | 18 August 1998 |
| 5,342,408 | DeCoriolis, et al. | 30 August 1994 |

All references listed in Table 1, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table 1 and elsewhere herein may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to telemetry systems for implantable medical devices. One of such problems involves the need to reduce power consumption for implantable medical devices. Further, for example, other problems include: the lack of flexibility in the movement of a programmer about the implant site without corrupting the data transferred; the complexity of implantable medical devices which include an antenna mounted within the case thereof; lack of accurate data being communicated between the implanted device and an external programmer; lack of a comfortable distance between patient and clinician when performing telemetry; the necessity of a lengthy time period in which the programmer must be held in a particular position to accomplish adequate and accurate communication; and the requirement for precise placement of an external device, e.g., a programmer head with respect to the implant site, to accomplish accurate communication.

In comparison to known techniques for providing telemetry for implantable medical devices, various embodiments of the present invention may provide one or more of the following advantages. For example, communication of information according to the present invention may be accomplished in a relatively reduced amount of time as compared to some conventional systems. The communication may be accomplished with an external device, e.g., a programmer head including an antenna of a programmer, positioned within a pre-defined communication volume of a patient without the need for the programmer head to be undesirably close to is the patient, without the need for the programmer head to be held in a particular position for an extended period of time, and without the need for placement of the programmer head in a precise position relative to the implant site. Further, the amount of power consumption may be reduced due to the substantially low current requirements necessary for providing telemetry according to the present invention. In addition, the communication system uses elements generally already existing in an implantable medical device, e.g. therapeutic leads, such that complexity and component part count is reduced, e.g., an antenna may be eliminated within the implantable medical device.

Some embodiments of the present invention include one or more of the following features: the provision of a modulated output signal generated by a transmitter of an implantable device into the body external of the housing of the implanted device such that the body functions as an antenna to radiate electromagnetic waves representative of the modulated output signal; the propagation of the modulated output signal in the body to radiate electromagnetic waves in a near-field communication volume surrounding the body; the generation of an asymmetrical current distribution within the body; the injection of the output signal into the body by way of a lead, e.g., therapeutic lead, extending from a position within the housing of the implantable device to a position external to the housing with the housing of the implantable device as a return path for the output signal; provision of a matching network for coupling the output signal into the body; a matching network for use in matching the impedance of the body; a receiver positioned within the housing of the implantable device for recovering data from modulated electrical signals resulting from the body functioning as an antenna and converting electromagnetic waves received thereby; a matching network for matching the impedance of the body, the matching network being part of a resonant circuit for providing a band pass filter for filtering received modulated electrical signals by the implantable device; establishing a communication link between the implanted device and an external communication device having an antenna when the antenna is at a first position within a near-field communication volume surrounding the body and moving the antenna of the external communication device anywhere within the communication volume without loss of the communication link; coupling the body to at least one of a transmitter and a receiver of an implanted device such that the body functions as an antenna for the implanted device to facilitate communication of data between the implanted device and an external communication device; an implantable device capable of telemetry including a matching network electrically coupling a transmitter positioned within the housing of the implantable device to a conductive element extending external of the housing with the matching network selected to match the impedance of the body; a matching network which when taken in combination with the body forms a resonant circuit having a quality factor (Q); a telemetry system including an external communication device having a receiver and/or transmitter connected to an antenna for receiving electromagnetic waves or transmitting modulated electromagnetic waves and also including an implantable device including a receiver and/or transmitter but with the body being used as the antenna for the implantable device; and an external communication device for receiving and/or transmitting within a communication volume surrounding the body which includes a three orthogonal axis antenna configuration.

DETAILED DESCRIPTION OF THE EMBODIMENTS

Figure 1:
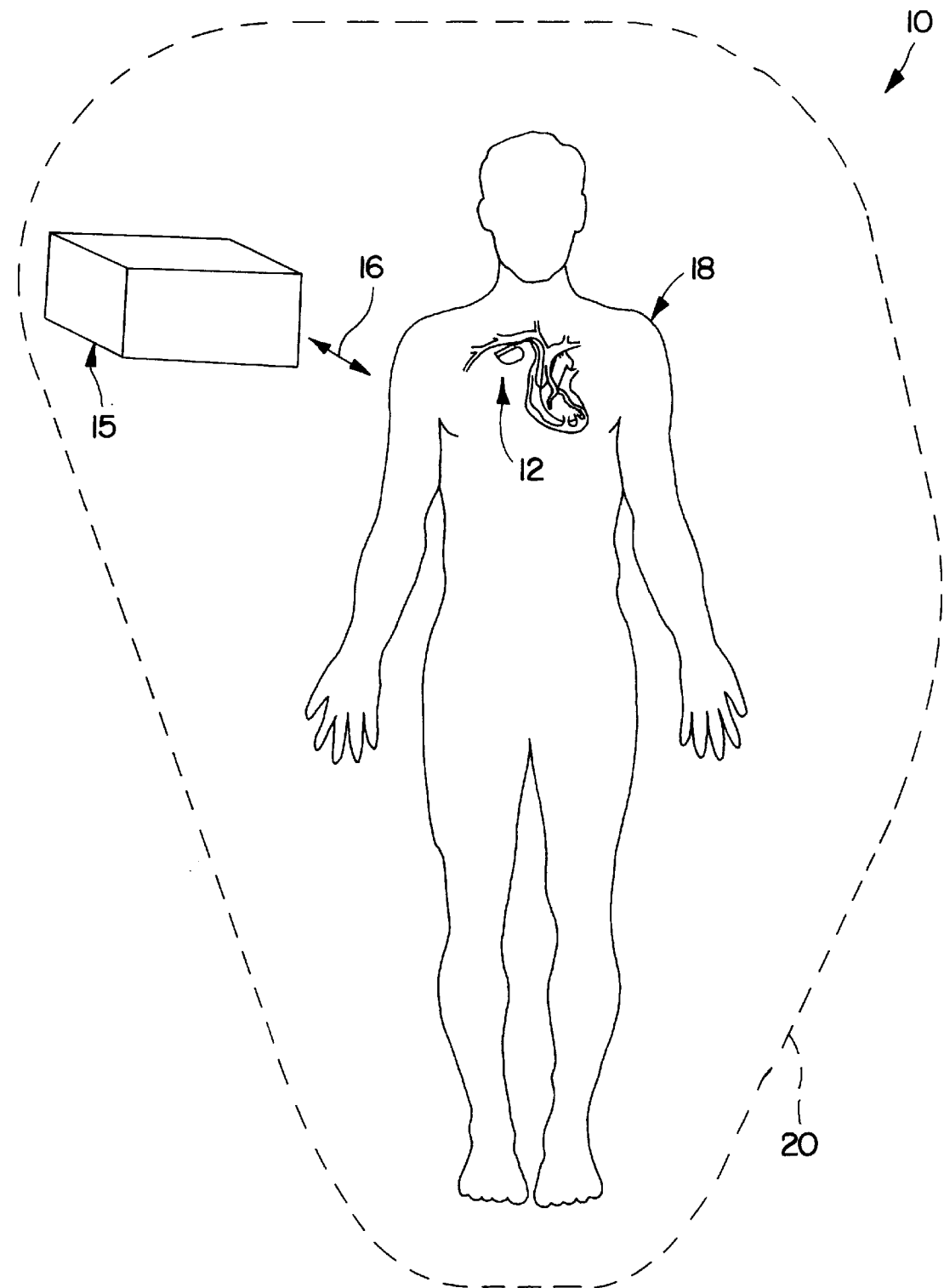
FIG. 1 is a diagram illustrating an implantable medical device in a body as part of a telemetry system according to the present invention.

FIG. 1 shows a telemetry system 10 according to the present invention for operation within a near-field communication volume 20 surrounding a body 18. The telemetry system 10 includes implantable device 12 and external communication device 15 which are operable for establishing a communication link 16 therebetween.

The present invention provides an effective bidirectional telemetry system 10 and method for communication between the implantable device 12 implanted in the body 18 and the external communication device 15, e.g., a programmer. The telemetry system 10 provides for effective telemetry while allowing for a greater range of distance between the implanted device 12 and an antenna of the external communication device 15 than conventional systems. Further, the system 10 provides for a desirable higher data rate and lower current drain than conventional systems.

The telemetry system 10 uses the body 18 as an antenna for the implanted device 12, e.g., the body 18 is used as the antenna in which an asymmetrical current distribution is generated such that electromagnetic waves are radiated from the body 18 into a near-field communication volume 20 surrounding the body 18. As the electromagnetic waves are radiated in the near-field communication volume 20, various advantages are attained as described herein. For example, the electromagnetic waves radiating from the body are not in a small zone surrounding the site at which the implantable device 12 is implanted, but are in the much larger near-field communication volume 20 surrounding the entire body. As such, an antenna of the external communication device 15 for receiving electromagnetic waves may be positioned and/or moved to various positions anywhere within the near-field communication volume 20 without interrupting a communication link 16 established between the external communication device 15 and the implanted device 12.

Figure 2:
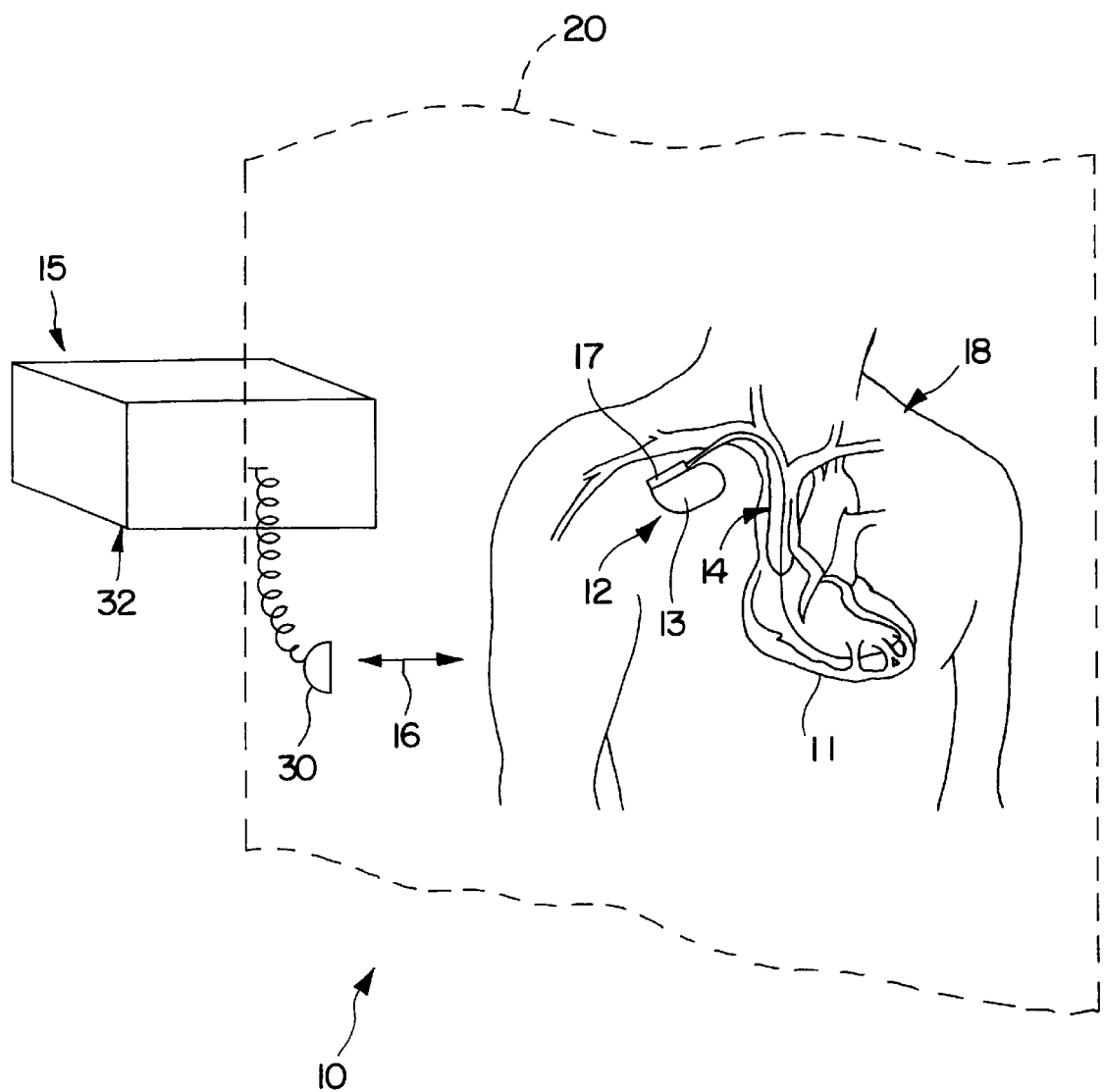
FIG. 2 is a more detailed view of the telemetry system of FIG. 1.
Figure 3:
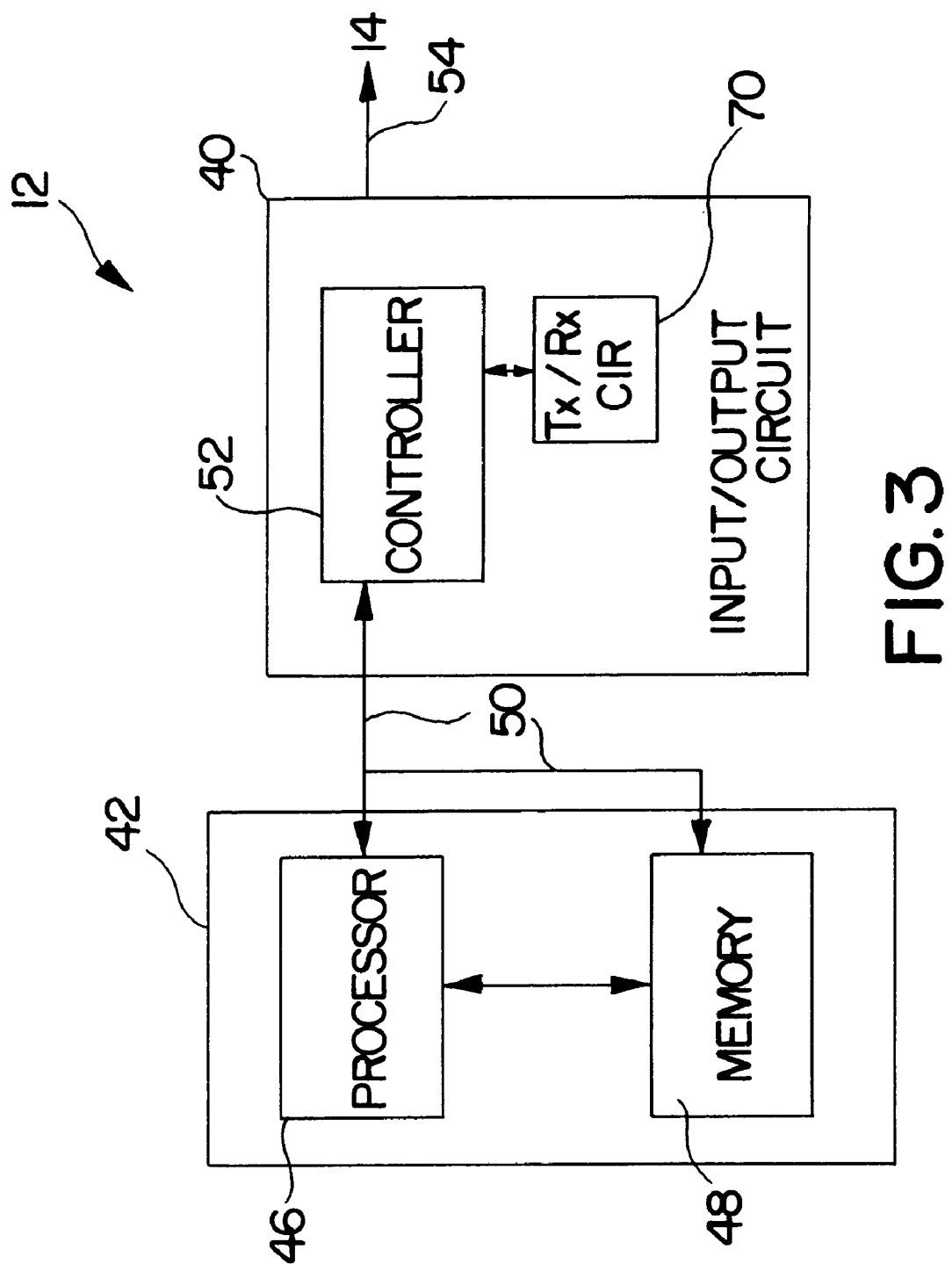
FIG. 3 is a general block diagram of circuitry of an implantable medical device including transmitter and receiver circuitry according to the present invention.
Figure 4:
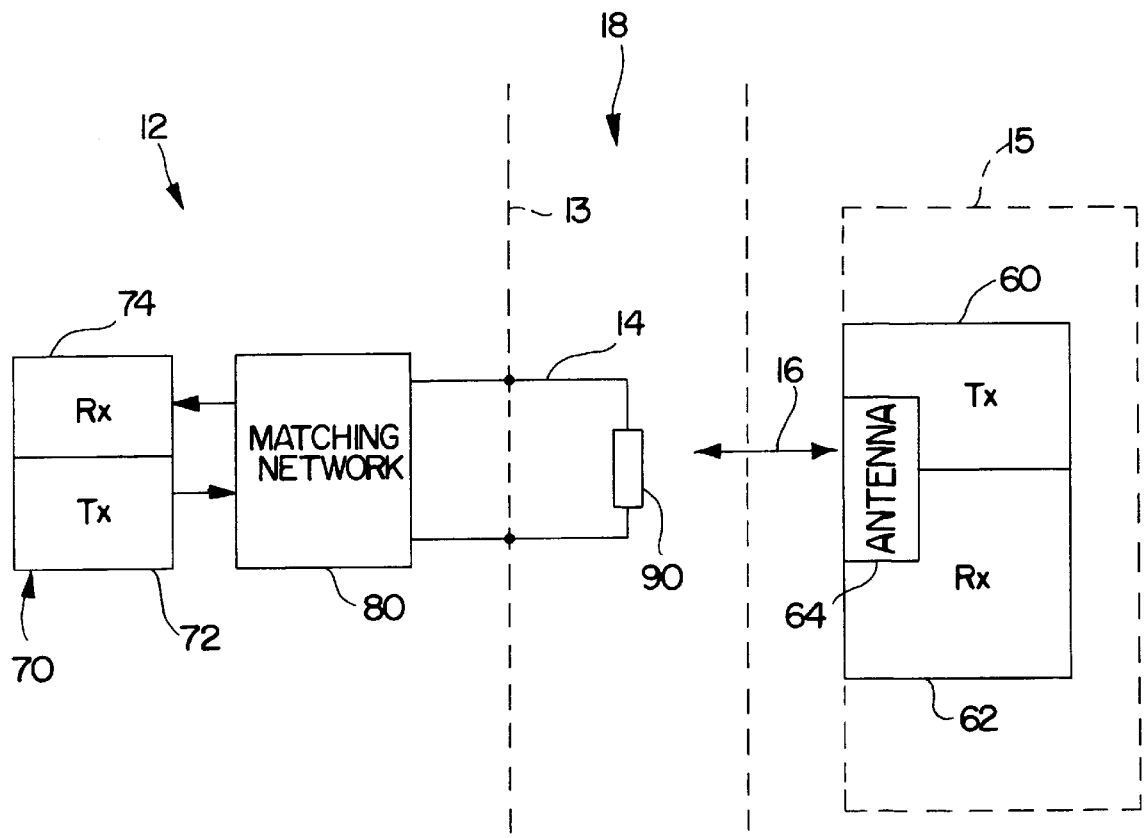
FIG. 4 is a general block diagram illustrating the telemetry system shown in FIGS. 1 and 2.

FIG. 2 is a more detailed view of the telemetry system 10 shown in FIG. 1. As shown in FIG. 2, implantable medical device 12 is implanted in body 18. Implanted device 12 includes a housing 13 in which components of the implantable medical device 12 are hermetically sealed, e.g., pacing circuitry, defibrillation circuitry, a battery, etc. Also positioned within the housing 13 is transmitter/receiver circuitry 70, as shown in FIGS. 3 and 4. At least one lead 14 is connected to the implantable medical device 12 in connector block region 17 such as with the use of feedthrough(s) (not shown). For example, the implantable medical device 12 may be implanted near a human heart 11. In the case where the implantable medical device 12 is a pacemaker implanted in the body 18, the pacemaker may include at least one or both of pacing and sensing leads represented generally as leads 14 to sense electrical signals attendant to the depolarization and repolarization of the heart 11, and to provide pacing pulses for causing depolarization of cardiac tissue in the vicinity of the distal ends thereof.

Generally, according to the present invention, the body 18 is used as an antenna for the implantable device 12 to radiate electromagnetic waves from the body 18 into the near-field communication volume 20 to be received by an antenna of the external communication device positioned within the near-field communication volume 20. The body 18 is provided with an output signal generated by a transmitter positioned within the implanted medical device 12. The output signal is propagated within the body 18 such that electromagnetic waves representative of the output signal are radiated therefrom. For example, an output current may be modulated by a transmitter to include data with the modulated output current injected from a distal end of a lead 14 into the body 18 and returned via the housing 13 of the implanted device 12. Due to the asymmetrical nature of the current distribution within the body 18 which functions as the antenna for the implanted device 12, a net magnetic moment arises as a consequence of this unbalanced condition, as shall be described further below with reference to FIG. 5. The magnetic field associated with the net magnetic moment in the near-field communication volume 20 provides for radiation of electromagnetic waves throughout the entire communication volume 20 surrounding the body 18 and not in any particular location relative to the implant site. The effectiveness of the body 18 as the antenna for the implantable device 12 is greatly enhanced over previous telemetry system antenna configurations because of the large area of the body available as the antenna source.

Generally, the communication volume 20 surrounding the body 18 in which communication is facilitated between the implanted device 12 and the external communication device 15, is preferably a volume within less than about 6 feet of the body. More preferably, the volume is substantially within less than about 3 feet of the body. The magnetic field generated in the communication volume 20 is generally stronger in the range of the site of the implanted device, e.g., stronger in the range of the torso when a cardiac pacemaker is implanted in proximity to the heart. The magnetic field generated drops off quickly because the magnetic component of the field is proportional to the distance from the source, i.e., the magnetic field drops off at a rate of $1/r^3$, where r is the distance from the magnetic field source, i.e., the body 18.

Therefore, as shown in FIG. 1, near-field communication volume 20 may be slightly larger around the implanted medical device site. However, the communication volume 20 does surround the entire body and propagation of electromagnetic waves in the volume 20 surrounding the entire body allows for a communication link to be established at any position in the communication volume 20 surrounding the body 18. In other words, although the distance that an antenna of the external communication device 15 may be positioned from the extremities of the body 18, e.g., feet, hands, etc., is generally less than such a distance closer to the implant site, a communication link 16 can still be established in the communication volume 20 about such extremities.

The telemetry system 10 allows for the employment of a highly efficient coupling configuration, as will be described further below with reference to the matching network of FIG. 4. The coupling configuration allows for use of a low output current to be injected into the body to be propagated therein, i.e., generating an asymmetrical current distribution within the body 18. Generally, the coupling configuration includes a matching network which in combination with the impedance of the body forms a resonant circuit having a quality factor (Q), preferably in the range of about 5 to about 15. More preferably, Q is in the range of about 7 to about 11. Although higher Q values may be implemented, higher Q values may result in tolerances which are to tight, e.g., receive bandwidth is to limited. The output current generated by the transmitter of the implanted device injected into the body is therefore multiplied by Q such that sufficient power is provided to the body functioning as the antenna to radiate electromagnetic waves into the communication volume 20. The electromagnetic waves radiated from the body are received by an antenna of external communication device 15, converted to electrical signals and the data being transmitted can be recovered by the receiver of the external communication device. For example, external communication device 15 may include a programmer apparatus 32 having a programmer head 30 electrically coupled thereto which includes an antenna that is movable within the near-field communication volume 20 so as to receive electromagnetic waves radiated from body 18.

Likewise, generally, the body 18 acts as an antenna for receiving electromagnetic waves generated in the near-field communication volume 20. For example, external communication device 15, as described further below with regard to FIG. 4, includes transmitter/receiver circuitry for generating modulated electrical signals for provision to an antenna of the external communication device 15 such that electromagnetic waves are radiated within the communication volume 20. The body 18 acting as the antenna for the implantable medical device 12 has a current distribution induced therein as a result of the received electromagnetic waves from the external communication device 15. Through use of the coupling configuration, i.e., matching network, which provides a band pass filter centered around an operating frequency, the transmitter/receiver circuitry of the implantable medical device receives and demodulates the modulated electrical signals induced in the body antenna representative of the electromagnetic waves radiated from the antenna of the external communication device 15.

It will be readily apparent to one skilled in the art from the description herein that the present invention need not be used as a bidirectional telemetry system, but may be used as a unidirectional system. In other words, external communication device 15 may only include a receiver to receive information from a transmitter of implantable device 12. Likewise, external communication device 15 may only include a transmitter for transmitting information to a receiver of implantable device 12.

Implantable device 12 may be any implantable device embodying the transmitter/receiver circuitry as described herein and using the body 18 as an antenna. For example, in the case where the implantable medical device 12 is a pacemaker, the implantable device may be a pacemaker such as that described in U.S. Pat. No. 5,158,078 to Bennett, et al.; U.S. Pat. No. 5,312,453 to Shelton et al.; or U.S. Pat. No. 5,144,949 to Olson et al.

Implantable medical device 12 may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson, et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable neurostimulator or muscle stimulator such as that disclosed in U.S. Pat. No. 5,199,428 to Obel, et al.; U.S. Pat. No. 5,207,218 to Carpentier, et al.; or U.S. Pat. No. 5,330,507 to Schwartz, or an implantable monitoring device such as that disclosed in U.S. Pat. No. 5,331,966 to Bennett, et al.

Further, for example, the implanted device 12 may be a defibrillator, a cardioverter/defibrillator, a brain stimulator, a gastric stimulator, a drug pump, a hemodynamic monitoring device, or any other implantable device that would benefit from telemetry capabilities. Therefore, the present invention is believed to find wide application in any form of implantable medical device. As such, the description herein making reference to any particular medical device is not to be taken as a limitation of the type of medical device which can use the body as at least a part of an antenna as described herein.

Generally, the implantable medical device 12 may have one or more leads 14 extending from the interior of the housing 13 to a position external to the housing 13. For example, the implantable medical device 12 may have multiple leads 14, each including one or more conductors for various therapeutic purposes including sensing physiological parameters, for use as stimulation electrodes, etc. For example, pacemakers are most commonly operated in conjunction with one or more leads for conveying cardiac stimulating pulses for the pacemaker to the patient's heart, and for conveying electrical cardiac signals from the heart to the pacemaker sensing circuitry. At least two different types of pacemaker leads, unipolar and bipolar, are commonly known and used.

Unipolar leads have only a single electrode and a single electrical conductor therein. Generally, the electrode is disposed at or near the distal end of the lead, which is situated in some particular location in the patient's body. For example, with respect to a pacemaker, the electrode may be situated in the patient's heart, e.g., at the apex of the heart in the right ventricle, in the atrial chamber, in the coronary sinus, etc. Further, the single electrode and conductor of a unipolar lead may be used both for sensing (that is, for conducting electrical cardiac signals from the heart to the pacemaker) and for pacing (that is, for delivering stimulating pulses from the pacemaker to the heart).

Bipolar leads have two electrodes and two electrically isolated conductors therein. Often, one electrode (called the "tip" electrode) is a conductive contact disposed at the distal end of the lead, while a second electrode (called the "ring" electrode) is a conductive ring disposed on the lead body some distance back from the distal end of the lead. For example, with respect to a pacemaker, one of the isolated conductors conducts signals between the pacemaker housing and the tip electrode, while the other conducts signals between the pacemaker housing and the ring electrode.

For simplicity, although various lead configurations are possible for the implantable medical device 12 as described herein, the remaining portion of the description herein shall be limited to the use of a single conductive element, e.g., a lead, extending from a position within the interior of the housing 13 to a position external to the housing 13. For example, such a lead may have a conductor extending through a feedthrough in connector block region 17. As further described in detail below, the present invention uses a conductive element located outside of the housing 13 of the implantable medical device 12 to provide electrical signals into the body 18. Such conductive elements used to provide the electrical signals into the body 18 may be an electrode or conductor of a lead 14 or may be any other element extending from the interior of the housing 13 of the implantable medical device 12 to a position external of the housing 13. Although the conductive element forms a small portion of the antenna in conjunction with the body, the size of the body relative to the conductive element makes it a minor portion of the antenna. As such, the body is referred to herein as being employed as the antenna although other minor antenna portions may actually exist, e.g., the conductive element used for providing the signal into the body and the conductive pacer housing.

Although the present invention is particularly described with reference to implantable medical devices, the present invention is in no manner limited to such medical applications. For example, the present invention may be used in any electronic application where a telemetry system is required and where use of the body as an antenna provides some advantage.

FIG. 3 generally illustrates a high level block diagram of constituent components of one embodiment of an implantable medical device 12, where the medical device 12 is implemented with a microprocessor-based architecture. However, the electronic features and operations of the implantable medical device 12 may be implemented in discrete logic or as a microcomputer-based system.

As shown in FIG. 3, the implantable medical device 12 includes a microcomputer circuit 42 including at least a processor 46 and memory 48. The microcomputer circuit 42 is coupled by a data communication bus 50 to a controller circuit 52 of an input/output circuit 40. For example, microcomputer circuit 42 may form a custom integrated circuit device augmented by standard RAM/ROM components. Further, for example, the input/output circuit 40 may include any other number of circuits in addition to the controller 52 such as is necessary for accomplishing the function of the implantable medical device 12. For example, the input/output circuit 40 may include sense amplifiers, peak sense and threshold measurement units, bias circuits, pulse generators, threshold detectors, etc., along with other input/output circuits such as those required to provide the controller 52 with appropriate signaling information. The specific embodiments of such circuits are not critical to the practice of the present invention so long as the circuits provide for generating signals corresponding to the desired implantable medical device and/or are capable of providing controller 52 with signals indicative of applicable physiological events, e.g., natural and stimulated contractions of the heart, and also so long as the implantable medical device 12 includes transmitter/receiver circuitry 70 according to the present invention for use in a telemetry system 10 as described herein.

Generally, the external communication device 15 shown illustratively in FIGS. 1–3 is an apparatus having at least transmitter/receiver circuitry 60 and an antenna 64 (as shown in FIG. 4) for transmitting and receiving electromagnetic energy. The external communication device 15 may be any programmer such as those used in telemetry systems for receiving information from an implantable medical device and transmitting information thereto. Generally, as previously described herein, such programmers are used to adjust parameters of implantable medical devices and typically have graphic displays, keyboards, or other user interfaces for data entry and device control by operator manipulation. Further, such programmers generally include printers or plotters to allow the user to control, evaluate, and document the extensive capabilities of the implanted device from which it is receiving information.

The external communication device 15 is compatible with the transmitter of the implanted device 12 and operable for receiving and demodulating the transmitted signal therefrom. Further, the external communication device 15 is compatible with the receiver of the implanted device 12 and operable for generating a modulated signal of which the receiver of the implanted medical device 12 is capable of receiving and demodulating. For ease of use, an antenna 64 is positioned within programmer head 30 connected to other components of the programmer apparatus 32 via a stretchable coil cable, although wireless communication or any other electrical connection is possible. The programmer head 30 is positioned within the near-field communication volume 20 such that the antenna 64 of the programmer head 30 receive electromagnetic waves radiating from the body antenna. However, one skilled in the art will recognize from the description herein that a programmer head including an antenna is not required for implementation of the system according to the present invention, but that the antenna may be a part of any type of external device 15, e.g., a transceiver device positioned in communication volume 20.

FIG. 4 shows a block diagram of the telemetry system 10 according to the present invention including implantable device 12 implanted in body 18 with a lead 14 extending from within housing 13 to a position external to housing 13. In addition, external communication device 15 is shown for establishing a communication link 16 with the implantable device 12. The external communication device 15, as previously described herein, includes transmitter circuitry 60, receiver circuitry 62, and an antenna configuration 64 for communicating with the implantable device 12 via body antenna 18. Implantable device 12 includes transmitter/receiver circuitry 70 and matching network 80. The transmitter/receiver circuitry 70 includes transmitter circuit 72 and receiver circuit 74. The matching network 80 couples the transmitter/receiver circuitry 70 to the body 18 which functions as the antenna. Although transmitter/receiver circuitry 70 is shown to include only transmitter circuit 72 and a receiver circuit 74, other circuitry for controlling such transmitter and receiver circuits 72, 74 also form a part of the implantable medical device 12, e.g., processors for controlling wakeup functions, controlling flow of data to the transmitter for modulation on a carrier signal, etc. In addition, other components of the implantable device 12, e.g., battery, provide power to such circuitry.

Generally, transmitter circuit 72 of the implantable medical device 12 includes a signal generator which generates an output signal that is modulated to include data to be transmitted to the external communication device 15. The modulated output signal is coupled into body 18 by the matching network 80. Preferably, the battery drive current required to drive the output of the transmitter circuit 72 is less than 50 micro amperes. More preferably, the battery drive current is in the range of about 5 micro amperes to about 50 micro amperes. For example, such battery drive current may be used for injection into the body of an output current in the range of about 10 micro amperes to about 300 micro amperes. Further, although the carrier or operating frequency of the output signal is not limited to any particular range, preferably, the frequency is less than about 25 MHz and greater than about 1 MHz. More preferably, the operating frequency is in the range of about 2 MHz to about 5 MHz. For example, the operating frequency may be in the frequency range of about 2.7 MHz. The use of a low frequency, however, may place undesirable restrictions on the possible data rate.

Further, preferably, the carrier output signal, e.g., a signal generated by an oscillator, is frequency modulated to include data. Preferably, frequency modulation is used, although phase modulation may also be used. Preferably, frequency shift keying (FSK) is used. Although any modulation technique may be used, frequency modulation or phase modulation are preferred over amplitude modulation because it is desired to keep the magnitude of the output signal low and also because they provide better rejection of interference. Further, preferably, an asynchronous protocol is used. However, any protocol, including synchronous communication may be used according to the present invention.

Preferably, the matching network 80 is selected to form a resonant circuit in combination with the impedance 90 of the body 18. The resonant circuit formed by the matching network 80 and the body impedance 90 preferably has a quality factor (Q) in the range of about 5 to about 15. As a result, the output current provided by the transmitter 72 is multiplied by the Q of the resonant circuit before the output current is propagated into the body 18. More preferably, Q is in the range of about 7 to about 11. In other words, the body 18 is tuned for very efficient operation as the tuned circuit, including the body, exhibits the properties of resonance.

Further, another way of describing the matching network 80 is that the matching network 80 is selected to match the body impedance 90 of the body 18. In other words, the power delivered by the output signal to the body 18 is performed with maximum efficiency and minimum distortion. By matching the body impedance 90 which functions as the antenna using the matching network 80 such that a resonant circuit is formed by the matching network and the body 18, a maximized output signal is coupled to the body 18. As described above, the output signal is generally multiplied by the Q of the resonant circuit.

Generally, body impedance 90 is dependant on at least the operating frequency, and also on the interface between the body and the conductive element, e.g., tip electrode, and the interface between the body and the return path, e.g., housing of the implanted device. For example, body impedance 90 may be in the range of about 50 ohms to about 500.

Figure 6A:
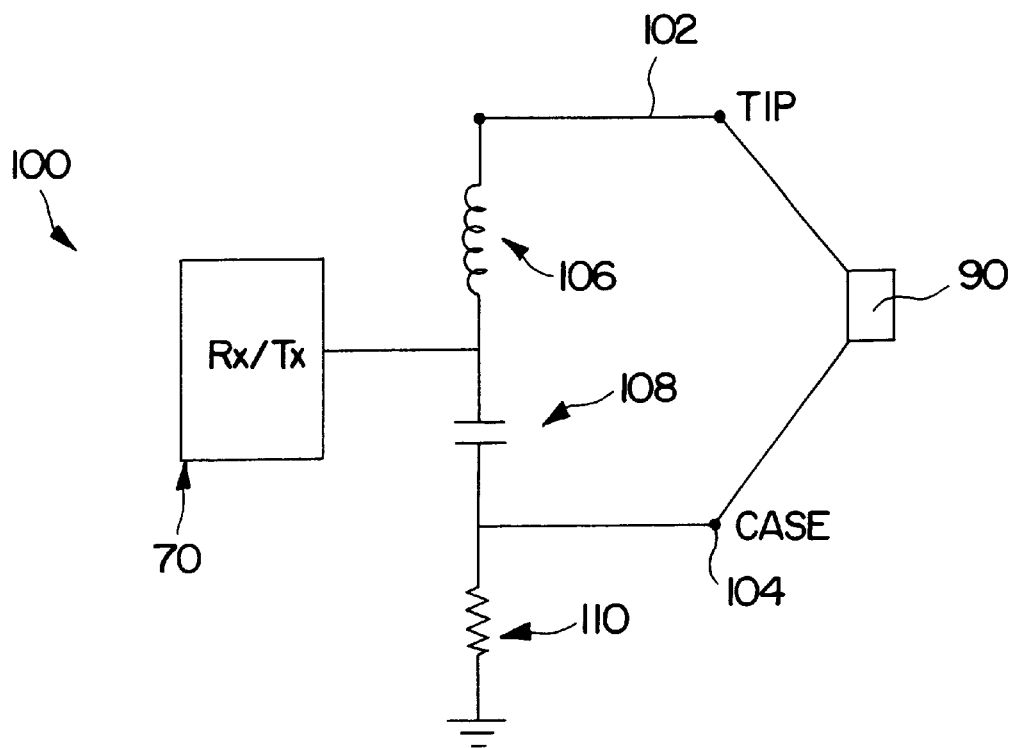
FIGS. 6A–6C are alternate embodiments of the matching network of the telemetry system illustrated in FIG. 4 for coupling the transmitter/receiver circuitry of the implantable medical device to the body according to the present invention.
Figure 6B:
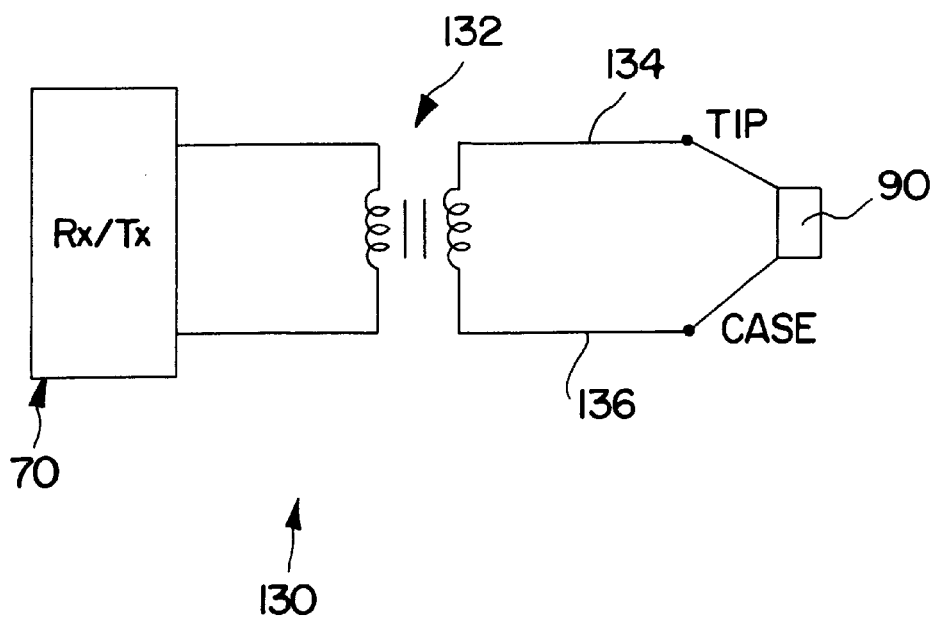
Figure 6C:
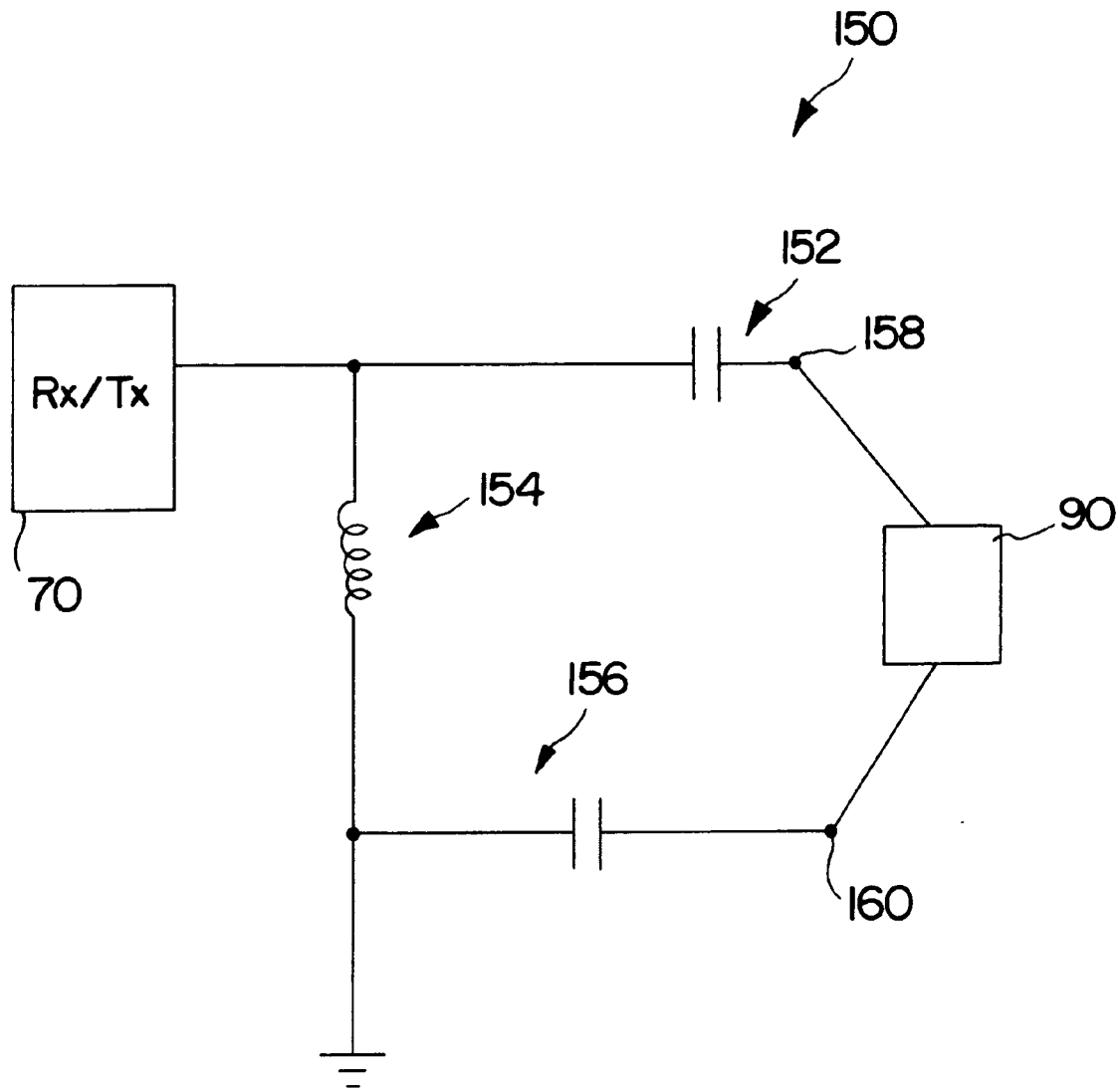

Various matching networks 80 may be used for coupling transmitter/receiver circuitry 70 to the body 18 which functions as the antenna for the implanted device 12. For example, as shown in FIG. 6A and FIG. 6C, matching network 80 may be provided using resistive, capacitive, and/or inductive components. As shown in FIG. 6A, a series resonant circuit is formed by matching network 100 including the inductor 106, capacitor 108, and resistor 110 connected relative to the body impedance 90. As shown therein, the transmitter/receiver circuitry 70 is connected between the inductor 106 and capacitor 108 serially connected between the tip electrode 102 and housing 104. The housing 104 is connected to ground via resistor 110.

Further, for example, as shown in FIG. 6C, a series resonant circuit is formed by matching network 150 including inductor 154 and capacitors 152, 156 connected relative to the body impedance 90. As shown in FIG. 6C, transmitter/receiver circuitry 70 is connected between capacitor 152 and inductor 154 which are connected with capacitor 156 in series between tip electrode 158 and housing 160. The housing 160 is connected through capacitor 156 to ground. An additional resistor may be connected between the housing 160 and ground in series with the capacitor 156.

One skilled in the art will recognize from the description herein, that many different configurations for matching network 80 to couple transmitter/receiver circuitry 70 to the body antenna may be used. Various configurations of matching networks for coupling transmitter/receiver circuits are known and may be use and/or modified to employ the body an antenna according to the present invention. For example, as shown in FIG. 6B, a transformer 132 may be used to couple the output signal of the transmitter/receiver circuit 70 into the body 18 between tip electrode 134 and housing 136 as shown by the matching network 130.

Figure 5:
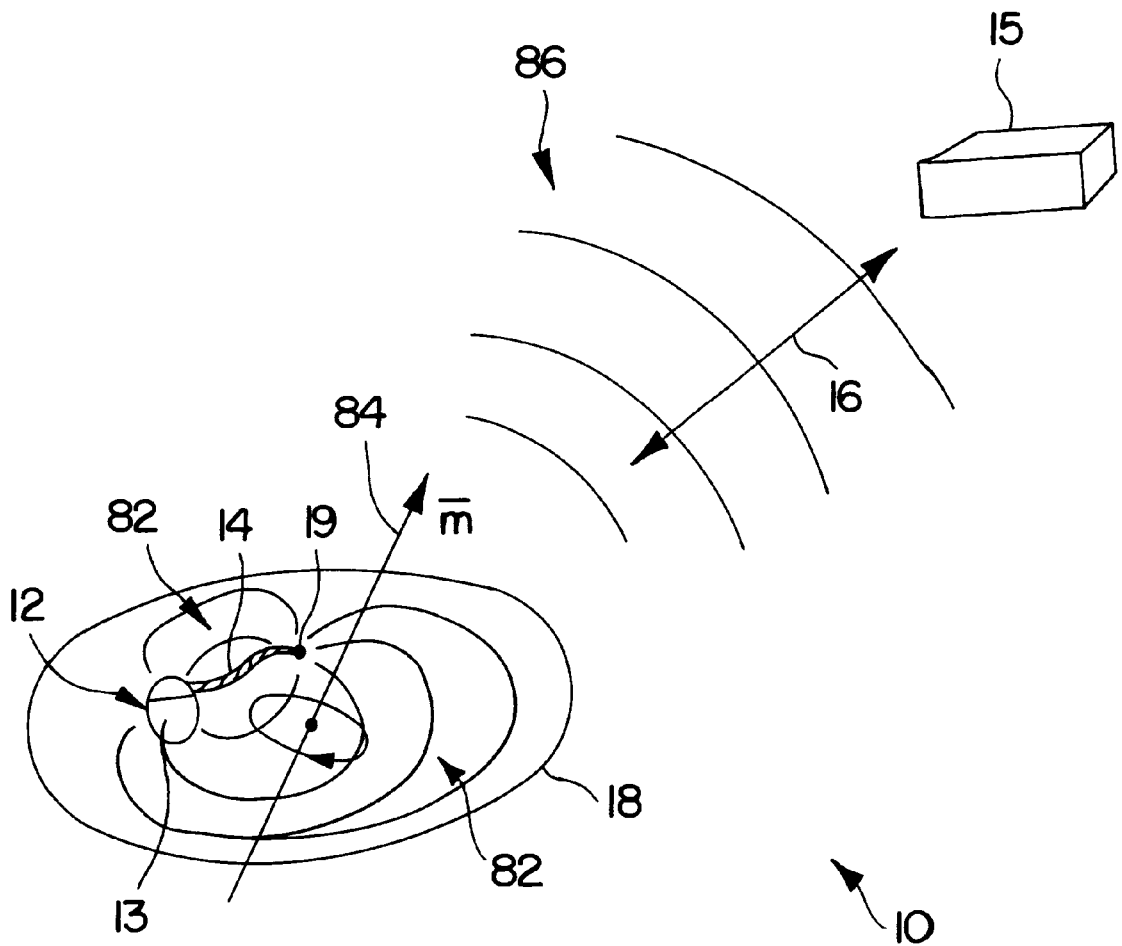
FIG. 5 is a general illustration of the telemetry system shown in FIGS. 1 and 2 for use in describing the manner in which the body functions as an antenna for the implantable medical device according to the present invention.

As shown in FIG. 5, as the output current from the transmitter circuit 72 of implantable medical device 12 is provided into body 18 at a conductive element such as the tip electrode 19 of lead 14, an asymmetric current distribution 82 is propagated within body 18. The asymmetric current distribution 82, e.g., including the current distribution lines shown in FIG. 5 between distal end 19 of lead 14 and housing 13 of implantable medical device 12, has a net magnetic moment vector 84 associated therewith.

It will be readily understood that the net magnetic moment vector 84 of the current distribution 82 shown in FIG. 5 is generally illustrative of the source of the magnetic field provided within communication volume 20. As the current distribution is asymmetric within the entire body 18, the strength of the magnetic field generated in the communication volume 20 will vary at different positions about the body 18. The magnetic field is generally strong enough to radiate electromagnetic waves 86 within the communication volume 20 such that external communication device 15 having an antenna positioned within the near-field communication volume 20 is operable for receiving such electromagnetic waves and such that data can be recovered therefrom.

The electromagnetic waves 86 propagated in near-field communication volume 20 by body 18 functioning as the antenna for the implanted device allows for antenna 64 of external communication device 15 to have electrical signals induced therein. The receiver circuit 62 of the external communication device 15 is operable and compatible with the transmitter 72 of the implanted device 12 such that the receiver 62 can detect, e.g., by filtering, the desired electrical signals provided by the antenna 64, e.g., a bandwidth signal including at least the carrier frequency of the output signal generated by the transmitter 72 of the implanted device 12. The receiver 62 further may include components for amplifying the received or detected signal and also demodulation circuitry compatible with the modulation circuitry of the transmitter 72 such that data modulated onto the carrier by the transmitter 72 can be recovered. In other words, the receiver circuit 62 may be any circuits as long as they are compatible for receipt and recovery of information from signals transmitted by transmitter 72. For example, if FSK modulation is used by transmitter 72 then FSK demodulation circuitry must be a part of receiver circuit 62.

The ability to couple a lower magnitude output signal from the transmitter circuit 72 into body 18, e.g., an output current in the 10 microampere to 300 microampere range, allows for telemetry to be performed without affecting other circuitry of the implantable medical device 12 or physiological characteristics of the body 18. For example, with such a low magnitude output, sense amps of a cardiac pacemaker would not signal a physiological event mistakenly.

Transmitter circuit 60 of external communication device 15 includes at least a signal generator for generating an output signal, e.g., an oscillator for generating a carrier signal, and modulation circuitry for modulating the output signal to include data. Like transmitter 72, any modulation technique is usable, although frequency modulation is preferred. Generally, the transmitter circuit 60 is compatible with receiver circuit 74 of the implanted device 12. In other words, for example, the modulation and demodulation techniques and operating frequencies are compatible. The transmitter circuit 60 provides the modulated output signal, including information or data, to antenna 64 for propagation of electromagnetic waves within the near-field communication volume 20 such that an induced electrical signal or current distribution is generated in the body 18 acting as an antenna for the implanted device 12.

The current distribution generated within body 18 is detected by receiver circuit 74 of implantable medical device 12 by way of the matching network 80 coupling the body 18 to the receiver circuit 74. As previously described, the matching network 80 and the body impedance 90 form a resonant circuit which provides a band pass filtering characteristic around the operating frequency. Such a resonant circuit has a Q preferably in the range of about 5 to about 15 which provides an associated bandwidth for filtering and detection of induced signals in the antenna created using the body 18. For example, with a Q in the range of 5–15, the bandwidth may be in the range of 600 kHz to 200 kHz. As is known, as the Q of the circuit increases, the associated bandwidth narrows. Receiver circuit 74 receives the filtered electrical signals in the region of the operating frequency representative of the modulated output signal generated by the transmitter circuit 60 of the external communication device 15 which includes data impressed thereon. The receiver circuit 74 recovers the data from the filtered electrical signals.

Generally, the receiver circuit 74 includes detection circuitry for detecting and amplifying a desired signal, i.e., the modulated signal including the carrier frequency. The modulated signal is provided to the receiver circuit 74 by the resonant circuit formed by the matching network 80 and the body 18 which provides the band pass filter characteristic centered at the operating frequency. Further, the receiver circuit includes a demodulation circuit compatible with the modulation circuit of the transmitter circuit 60 to recover the data modulated onto the carrier output signal.

Therefore, generally, in both uplink and downlink communication directions, the body 18 functions as an antenna for the implantable medical device 12. It is the function of the body 18 as the antenna which provides the advantages described herein. The matching network 80 selected for matching the impedance of the antenna, i.e., the body 18, forms a series resonant circuit with the body antenna such that the modulated output signal from the transmitter circuit 72 of the implanted device 12 is multiplied and sufficient power is provided to the body for radiation of electromagnetic waves therefrom. This allows for a lower power consumption by the implantable medical device 12 as the battery drive current necessary for driving the output of the transmitter circuit 72 can be kept low, e.g., in the 5 to 50 microampere range.

Various data rates may be established for the communication link 16 and the present invention is not limited to any particular data rate. In one illustrative embodiment, the uplink data rate is about 57 kilobits/second. As there is generally not as much data to be transferred downlink, i.e., from the external communication device 15 to the implantable medical device 12, the downlink data rate may be much less than the uplink rate. For example, in one illustrative embodiment, the downlink data rate is about 9.6 kilobits/second.

The communication channels established by the communication link 16 between the external communication device 15 and the implantable medical device 12 may be varied in the number of channels of data transferred. For example, the stream of data being transmitted may be transmitted using a four-channel communication link, a five-channel communication link, etc. Preferably, data is transferred asynchronously by packeting the data along with error code. Further, open space is left in the channel to allow for the receivers time to look for incoming data. In other words, data is not transferred in both directions simultaneously, but rather data is transferred in one direction with a receiver periodically looking for information from the transmitter of the other device. Various types of transmission links can be established between the implanted device 12 and the external communication device 15, and the present invention is not limited to any particular transmission technique but is limited only to the use of the body 18 as an antenna for the implanted device 12 to establish such links.

Figure 7A:
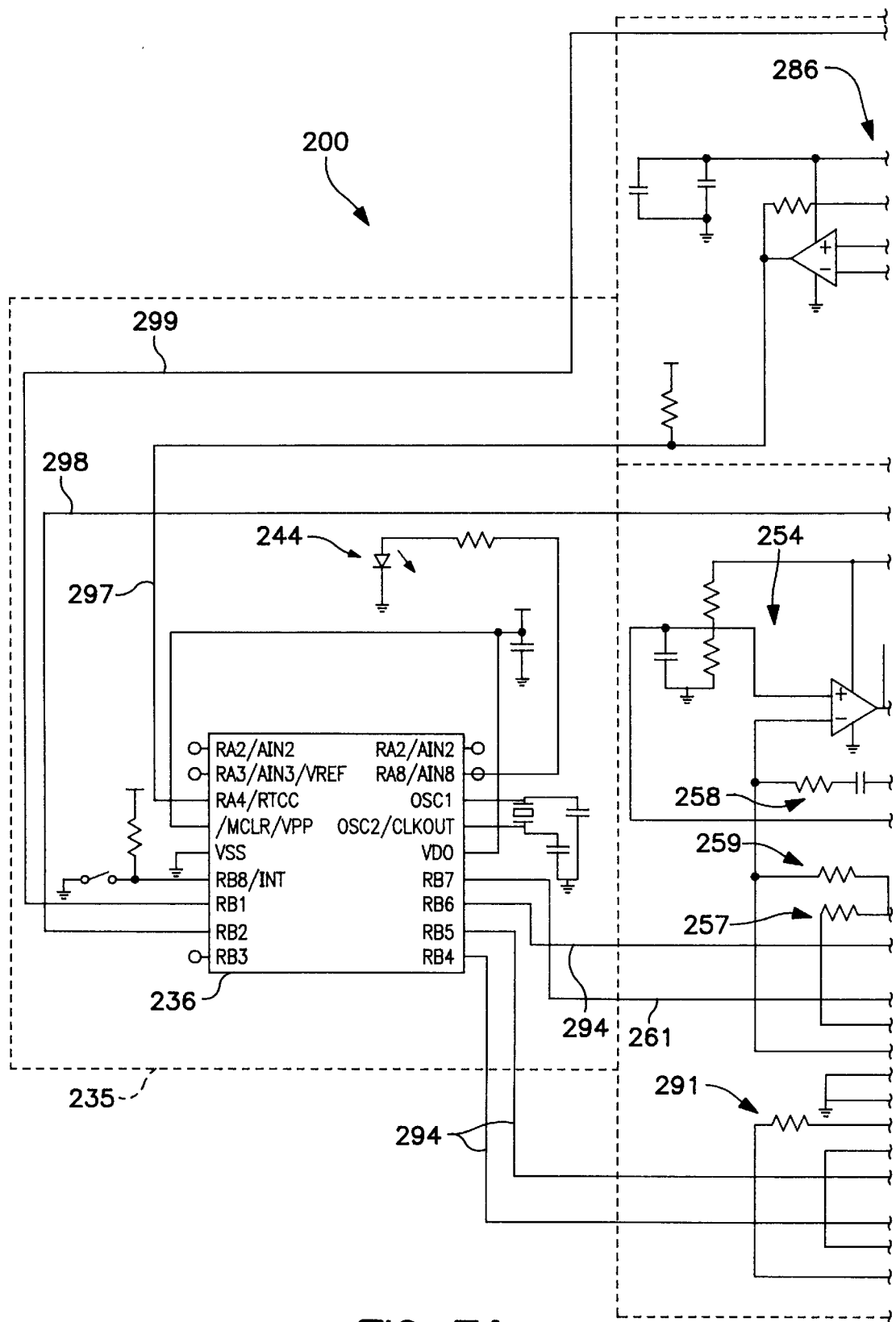
FIG. 7 is a schematic diagram of one embodiment of transmitter/receiver circuitry and a matching network of the implantable medical device illustrated in FIG. 4 according to the present invention.
Figure 7B:
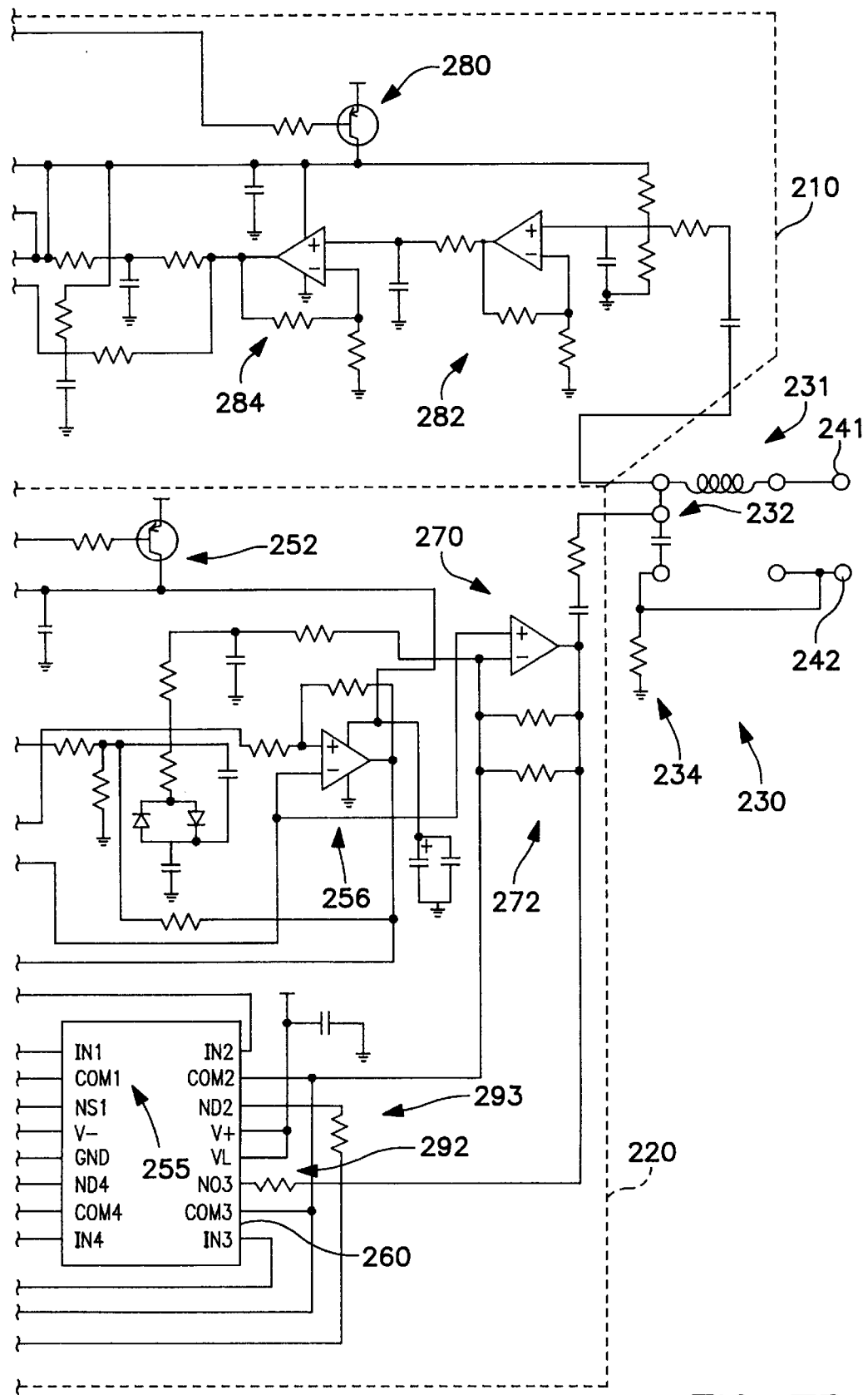

FIG. 7 is one embodiment of transceiver/receiver circuitry 70 generally shown in FIG. 4. The transceiver/receiver circuitry 200 shown in FIG. 7 is electrically coupled to a tip electrode 240 and housing 242 of the implantable medical device 12 by matching network 230. The transceiver/receiver circuitry 200 includes receiver circuit 210, transmitter circuit 220, and microcomputer 235. Both receiver circuit 210 and transmitter circuit 220 are coupled to the body 18 using matching network 230. The matching network includes an inductor 231 connected between the transmitter and receiver circuits 220, 210 and tip electrode 240. A capacitor 232 is connected between transmitter and receiver circuits 220, 210 and housing 242 of the implanted device 12. Housing 242 is connected to ground through resistor 234. Preferably, in this illustrative embodiment, the transmitter/receiver circuitry 200 is provided for operation at 2.7 MHz.

Control of the transmitter/receiver circuitry 200 is performed by microcomputer 235. For example, the microcomputer 235 may include a microcomputer component 236, such as a Microchip PIC 16C71. The microcomputer 235 is put to sleep about five minutes after any activity. A "watchdog timer" in the microcomputer 235 wakes up the microcomputer approximately every two seconds, e.g., 1.8 seconds, and the receiver circuit 210 is turned on to listen for a carrier signal being received by the body 18. If a carrier signal is detected, the transmitter/receiver circuitry 200 is set in an active mode. When a carrier is detected, the LED 244 is turned on. The LED 244 is provided for test purposes only and generally would not be part of an implanted device. Because of the low current requirements of the circuitry 200, the receiver circuitry may be kept continually on for long periods of time, and even possibly continually on over the life of the device.

Power to the transmitter circuit 220 is controlled by the microcomputer 235 through transistor 252 via transmitter on/off control line 298. When power is applied, amplifier 254 and comparator 256 form an oscillator configuration with capacitor 258 and resistor 259 determining the frequency of oscillation, e.g., 2.7 MHz.

The frequency of the oscillator configuration is modulated by frequency shift keying (FSK) using one section 255 of the analog switch 260 under control of microcomputer 235 via "0"/"1" select line 261. The frequency is modulated between "0" and "1" by switching resistor 257 into and out of the oscillator configuration.

Amplifier 270 amplifies and buffers the output of the oscillator configured using amplifier 254 and comparator 256 to drive the antenna through the matching network 230. Resistors 291–293 are used to select the output level of the transmitter circuit 220 under control of microcomputer 235 via output select lines 294. Such resistors 291–293 are used to control the gain of amplifier 270 in conjunction with parallel resistors 272.

Power to the receiver circuit 210 is controlled by the microcomputer 235 through transistor 280 via receiver on/off control line 299. The receiver circuit 210 uses two stages of amplifiers 282, 284 to amplify the signal received. For example, the amplifiers 282, 284 may each provide a gain of about 11. Comparator/amplifier 286 of a third stage provides additional gain and digitizes the signal for input to the microcomputer 235 via input line 297.

The microcomputer 235 demodulates the FSK incoming signal from the receiver circuit 210. To perform the demodulation, an internal counter is used to determine the frequency of the incoming signal. Data is then decoded from the frequency determined. Generally, a universal asynchronous receiver/transmitter (UART) is implemented by microcomputer 235 to decode the incoming data. When a predetermined byte of the incoming data is received and decoded by the microcomputer 235, the power level of the transmitter circuit 220 is selected and a response is transmitted back through transmitter circuit 220 to the external device 15. For example, the response may be a short message which includes the same byte or a continuous carrier may be transmitted.

One skilled in the art will recognize from the description herein that various transmitter/receiver circuitry configurations may accomplish the advantages described herein. For example, advantages may include providing a small current output, use of minimum power, etc. As such, the present invention is not limited to the particular configuration illustrated herein.

FIGS. 8A–8B and 9A–9B illustrate embodiments of an antenna configuration and transmitter/receiver circuitry for an external communication device 15 according to the present invention. Generally, as previously described herein, the magnetic field surrounding the body 18 is a near-field and has detectable magnitude everywhere in the vicinity of the body 18. Although use of the body as the antenna provides a magnetic field in the communication volume 20 surrounding the body 18, if a single axis element antenna configuration, e.g., a single coil antenna, is used in the external device 15, then there may be null positions of the antenna where communication between the external device 15 and the implanted device 12 is difficult, e.g., appreciable signal is not received by the antenna. With use of an omnidirectional antenna system as described herein with reference to FIGS. 8A–8B and 9A–9B, null positions of the antenna in the communication volume 20 are eliminated and a continuous link is assured between the transmitter/receiver circuitry of the external communication device 15 and the transmitter/receiver circuitry of the implantable device 12.

Although a single antenna element configuration, e.g., an antenna having a single axis such as a single coil antenna, can be used in combination with the magnetic field provided in the communication volume 20 established by using the body as an antenna according to the present invention, the use of three orthogonal antenna elements each orientated along one of three orthogonal axes (i.e., x, y, z) as described with reference to FIGS. 8A–8B and 9A–B eliminates the possibility of potential communication nulls. Further, in one embodiment, selection of one of the three orthogonally oriented antenna elements based on the strength of the signals received thereby for use in providing the signal received from the body antenna to the transmitter/receiver circuitry of the external communication device 15, and for use in providing transmission into the communication volume 20, assures that a strong link is established.

Figure 8A:
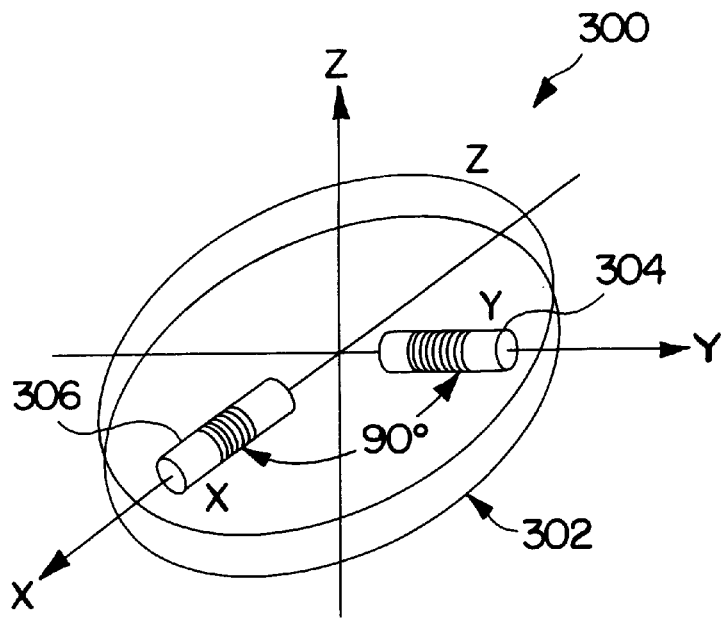
FIGS. 8A–8B are illustrative diagrams of one embodiment of an antenna configuration and transmitter/receiver system for an external communication device shown generally in FIG. 4 according to the present invention.

One illustrative three orthogonal axis antenna configuration 300 is shown in FIG. 8A. The antenna configuration 300 includes an air core circular antenna 302 having a z axis extending through the center thereof. Further, the antenna configuration 300 includes two ferrite antennas 304, 306. Ferrite antenna 304 has a y axis extending longitudinally therethrough and antenna 306 has an x axis extending longitudinally therethrough. Various antenna arrangements are possible and the present invention is not to be taken as limited to this particular configuration but only to the configuration where a three orthogonal axis antenna is provided. For example, all three antenna components could be air core circular antenna elements, all three antenna components could be ferrite core elements, or such antenna components could be any combination of air core circular elements, ferrite core elements, or any other types of antenna elements.

Figure 8B:
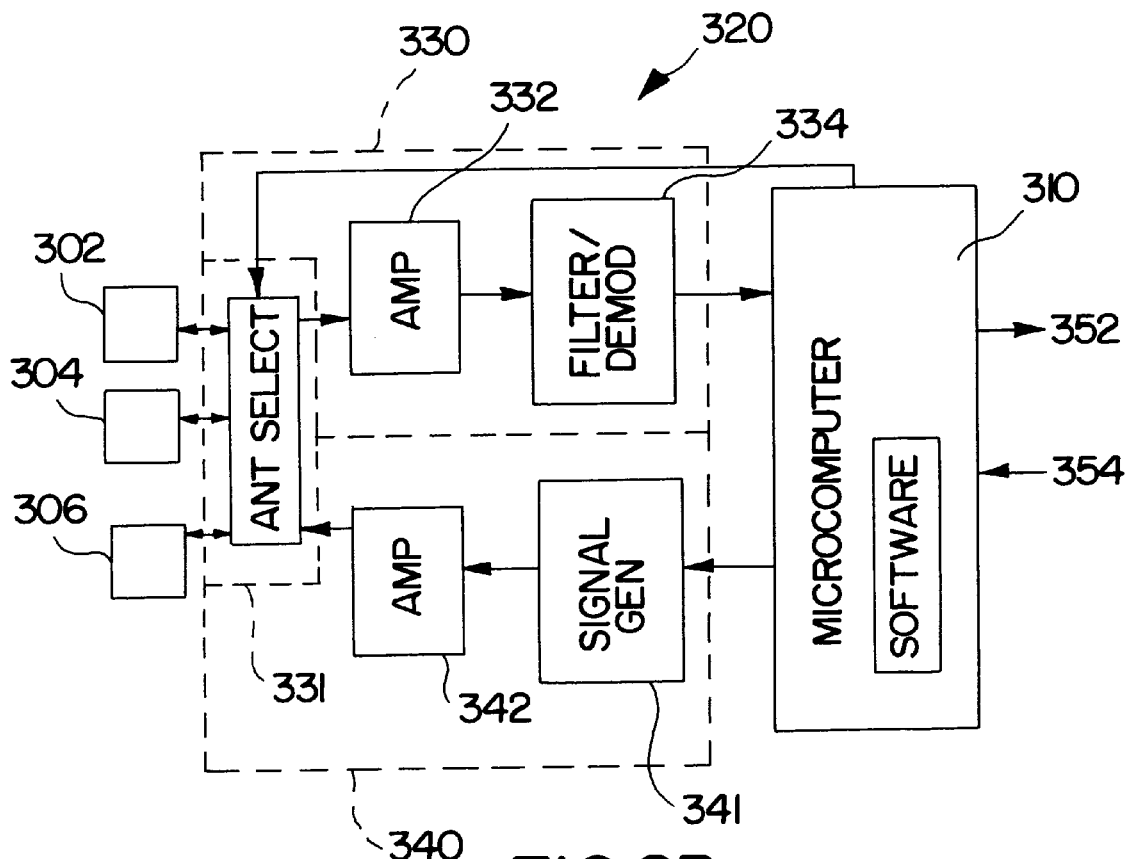

A transmitter/receiver system 320 and method for use with the three orthogonal antenna configuration 300 is shown in FIG. 8B. The system 320 includes microcomputer 310, receiver circuitry 330, transmitter circuitry 340, and antenna select circuitry 331. With respect to receiving radiated electromagnetic waves from the body used as the antenna, each of the antenna elements 302, 304, 306 has a current signal induced therein. The current signals of each antenna element 302, 304, 306 are selectively provided, e.g., via polling, to the receiver circuitry 330 under control of the microcomputer 310 through use of the antenna select circuitry 331. Each selected signal is amplified by an amplifier section 332 of the receiver circuitry 330 to provide a bandpass about the operating frequency. The amplified signals are then further filtered, demodulated, and converted from analog signals to digital signals by demodulation circuitry 334. At the same time the strength of each selected signal from each of the antenna elements is determined and provided to microcomputer 310. Microcomputer 310 implements a software routine to select the strongest of the three antenna element signals. The signal from the particular antenna which is providing the strongest signal is provided for demodulation and decoded by a UART implemented by software in the microcomputer 310 to generate data output 352.

With regard to the transmittal of electromagnetic waves into the communication volume 20 by the system 320, the system 320 also polls the antennas to select the antenna element which has received the strongest signal from body antenna. Under control of the microcomputer 310, a signal generator 341 of the transmitter circuitry 340 modulates an output signal to include data. The modulated signal is amplified by an amplifier section 342 of the transmitter circuitry 340. Just like in selection of an antenna for use in receiving uplink information, the strength of a signal transmitted by the implanted device 12 is polled at the three antenna elements 302, 304, 306 and a transmit antenna is selected based on the strengths thereof. As such, the antenna which produces a signal in the communication volume 20 which will be suitably received by the implanted device 12 is selected.

Polling of the three orthogonal antenna elements 302, 304, 306 ensures selection of the appropriate antenna to provide the strongest link between the implanted device 12 and the external device 15 as the programmer head is moved in the communication volume 20. One skilled in the art will recognize that received signals from more than one of the antennas may be combined to produce a stronger signal, although this variation to the basic concept uses more complex combination algorithms in the microcomputer 310, e.g., signals form the antenna may be squared and summed with the square root of the sum providing a very strong signal. Use of three orthogonal antennas elements is described in various publications. For example, three orthogonal antennas are used and described in the article entitled, "Improve the Reading Distance of Omnidirectional RFID Systems," by Angelo et al., *Microwaves & RF* (August 1995), and the book entitled "Biomedical Telemetry" by C. A. Caceres, pgs. 152–235, *Academic Press*, New York and London (1965). However, such publications do not describe the use of such an antenna configuration in a telemetry system for an implantable medical device wherein the body is used as the antenna for the implanted device. Further, a selection technique as described herein is not provided in such publications.

Figures 1, 9A:
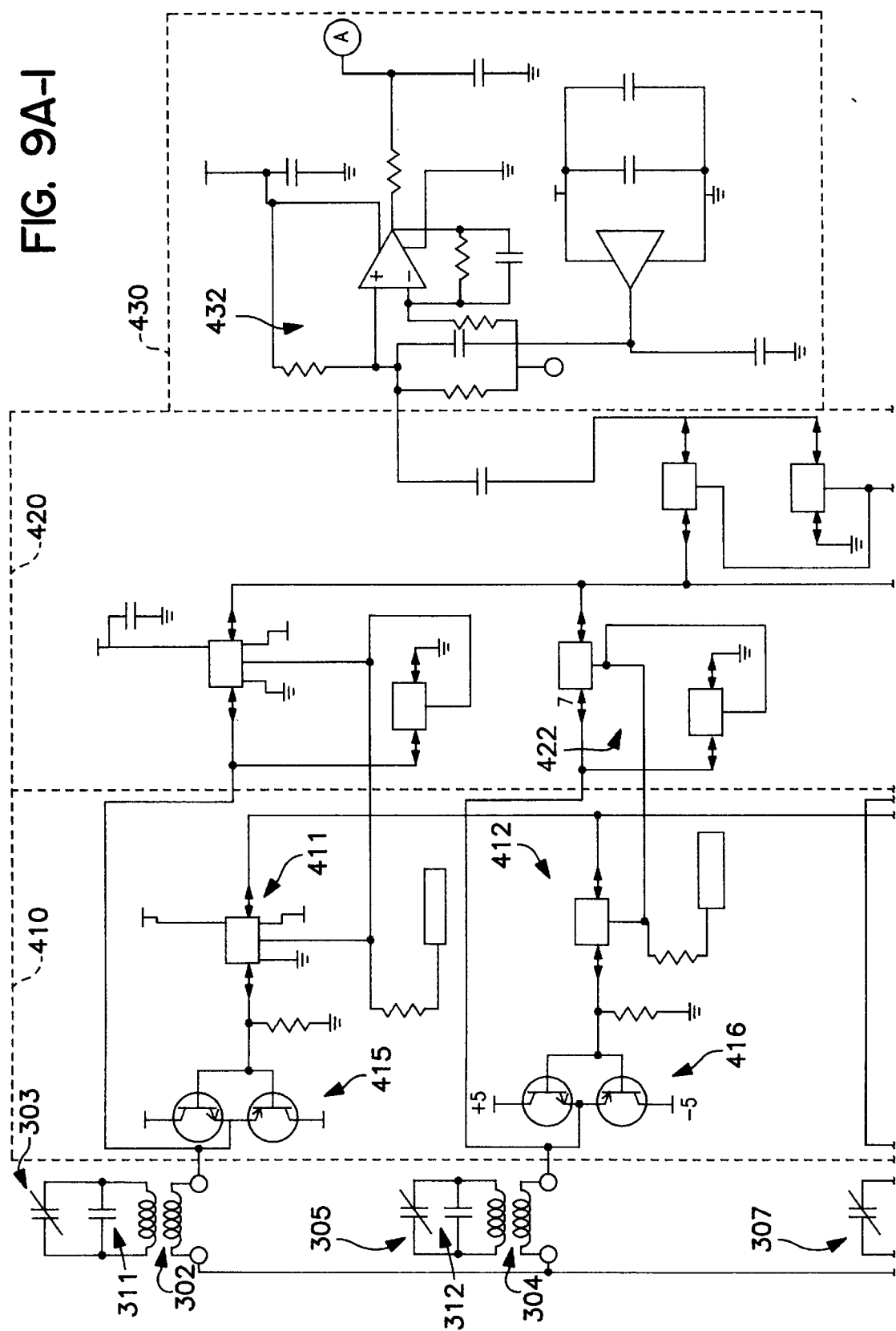
FIGS. 9A–9B are a schematic diagrams of one embodiment of transmitter/receiver circuitry of an external communication device shown generally in FIGS. 8A–8B.
Figures 2, 9A:
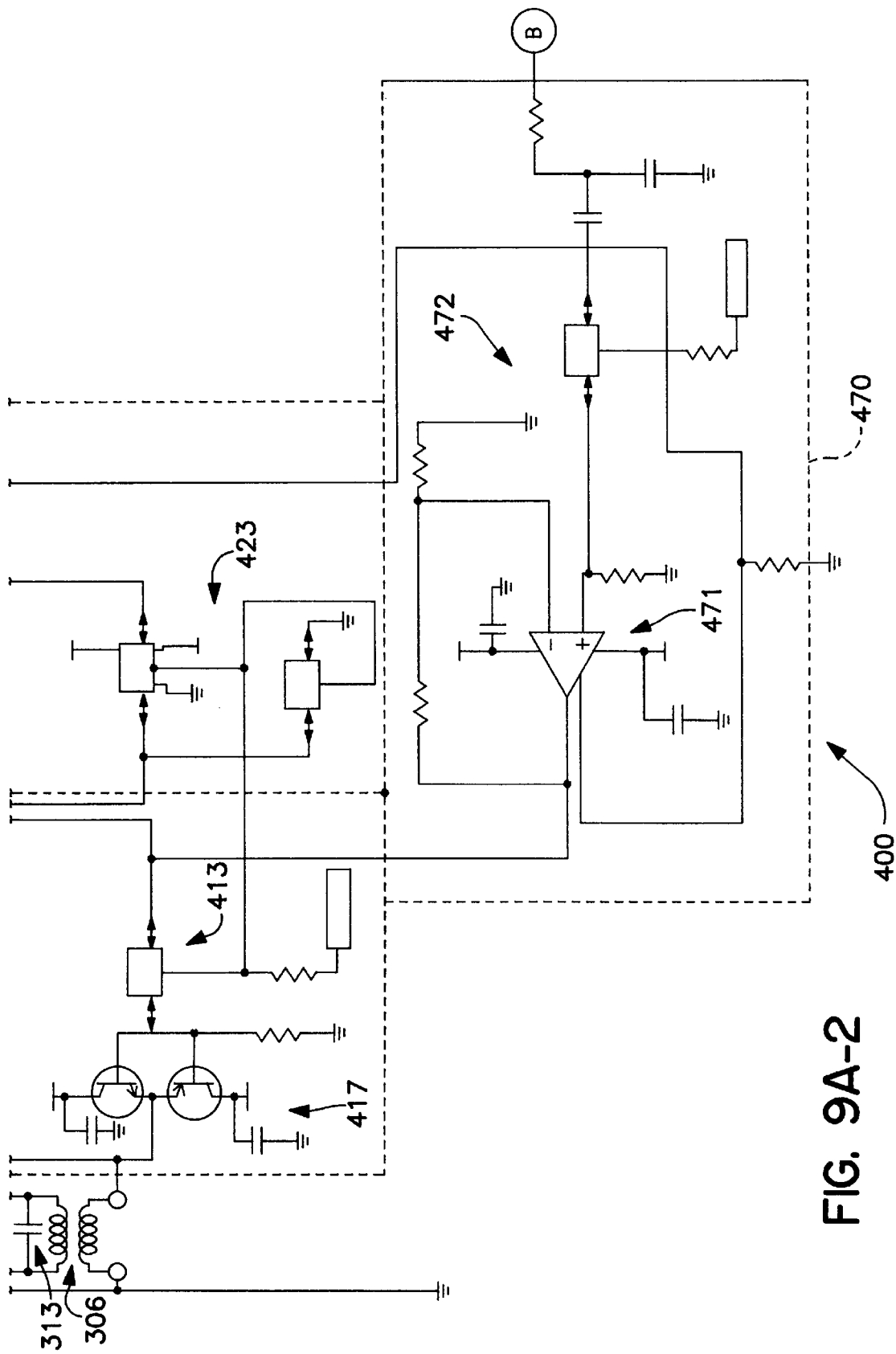
Figures 1, 9B:
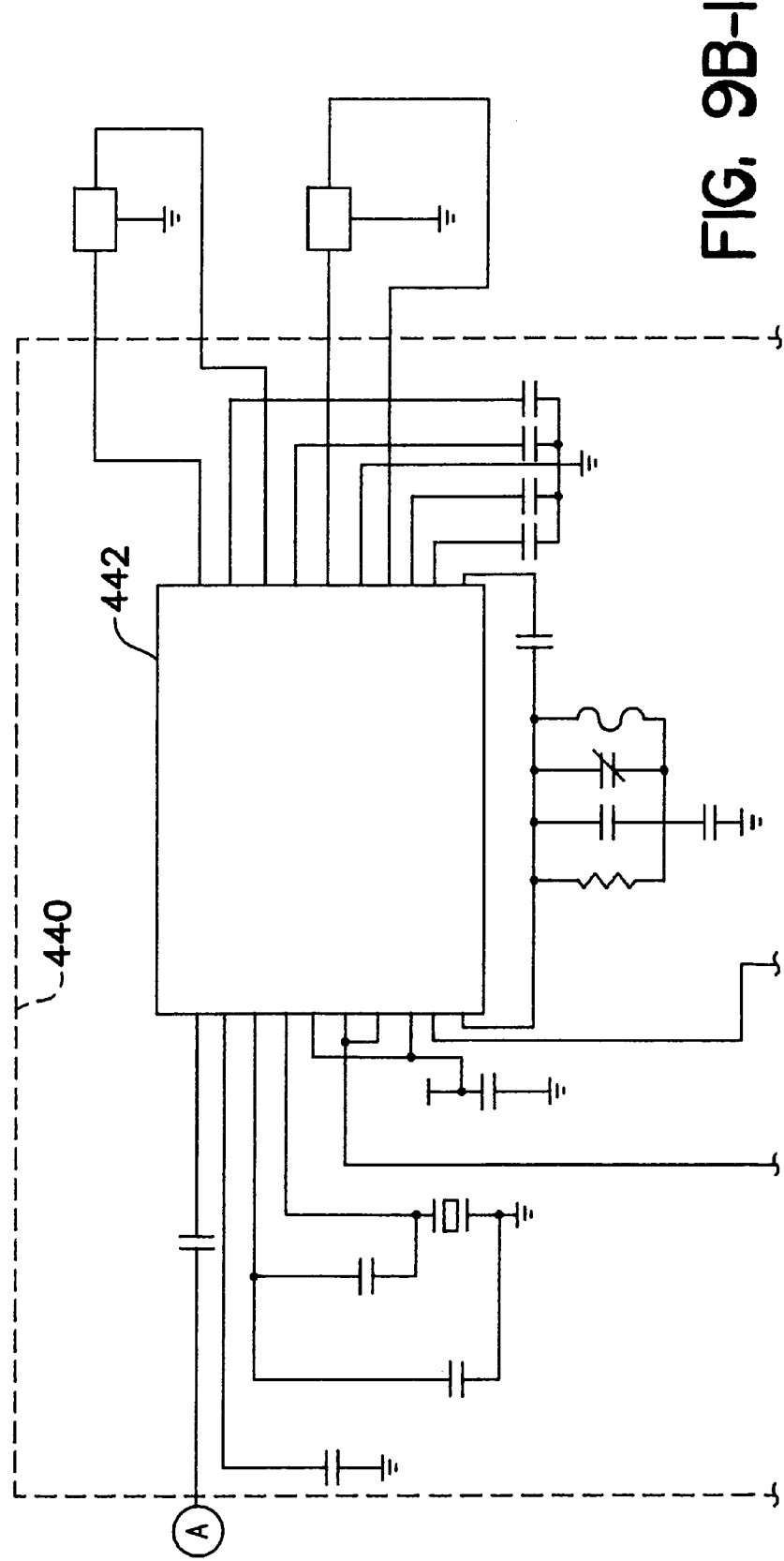
Figures 2, 9B:
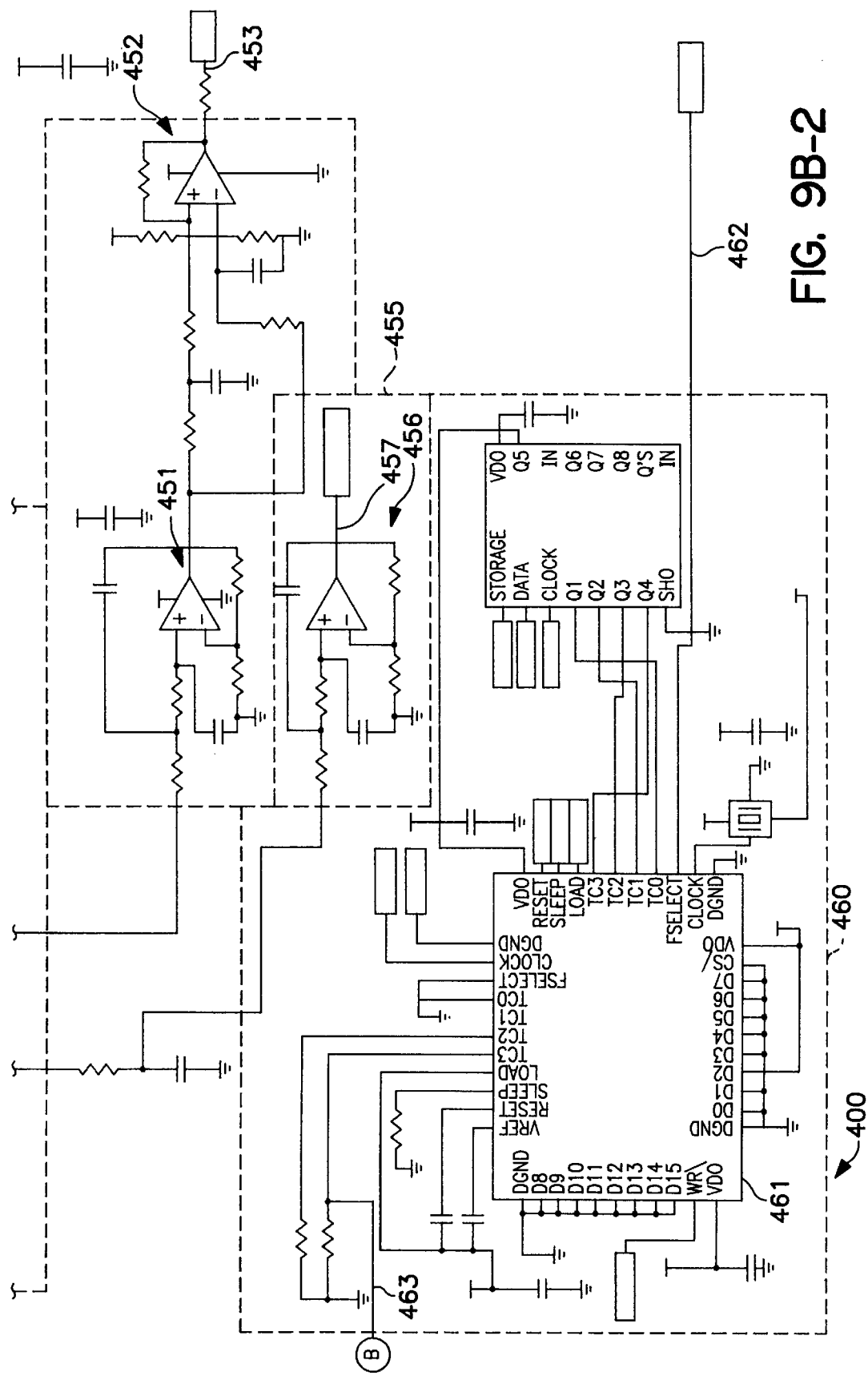

FIGS. 9A–9B are schematic diagrams of one embodiment of a three orthogonal antenna configuration 302, 304, 306 coupled to transmitter/receiver circuitry 400 of an external communication device 15. For example, the operating frequency of the transmitter/receiver circuitry 400 may be 2.7 MHz which coincides with the operating frequency selected for the transmitter/receiver circuitry described with reference to FIG. 7. The uplink data rate, i.e., from the external communication device 15 to the implantable medical device, may be 57.6 kbits/second. The downlink data rate may be 9.6 kbits/second. The modulation technique used is FSK, the same technique as the transmitter/receiver circuitry shown and described with reference to FIG. 7. The protocol for the transmission is asynchronous. However, with respect to any embodiment herein, synchronous protocol may also be implemented.

The transmitter/receiver circuitry 400 is controlled by a microcomputer (such as shown in FIG. 8B, but not shown in FIG. 9A–9B). The transmitter/receiver circuitry 400 includes analog switch/output drive circuitry 410, antenna selection circuitry 420, receiver front end circuitry 430, filter/demodulator circuitry 440, discriminator circuitry 450, signal strength indication circuitry 455, transmit signal generator 460, and transmitter output amplifier circuitry 470.

The microcomputer (not shown in FIGS. 9A–9B) may be any microcomputer such as an 8-bit device, e.g., a Microchip PIC 16C74A, which includes a UART. All control and data handling is performed by the microcomputer. A data logic control device (not shown) may be in the data path from the UART of the microcomputer to the transmitter/receiver circuitry data input and data output, and also from the UART to an external serial port, allowing for the switch in direction of the data flow, i.e., from uplink to downlink and vice versa. A display (not shown), which may have an integrated controller, may be driven by the microcomputer (not shown).

To implement the telemetry receiver, selection from among the three orthogonal antennas 302, 304, 306 is made with analog switches 421–423 of the antenna selection circuitry 420 under control of the microcomputer. Each switch of the analog switches 421–423 includes a normally open and a normally closed section. This allows the two antennas that are not selected to be shorted so as to minimize coupling effects.

The receiver front end 430 includes a low noise amplifier 432 having a gain, for example, of about 20. The amplified signal feeds a standard superheterodyne receiver 442 of the filter/demodulator circuitry 440. Ceramic IF filters with a nominal bandwidth of 180 KHz are used to set the optimal bandwidth for the uplink data rate.

The discriminator circuitry 450 for implementing the telemetry receiving function is used to demodulate the FSK signal provided by the superheterodyne receiver 442. An amplifier 451 of the discriminator circuitry 450 is used to filter and amplify the signal. The amplified signal is then fed to a comparator 452 which functions as an adaptive slicer to digitize the data signal. The signal 453 is available for decoding by the UART of the microcomputer.

Operational amplifier 456 of signal strength indication circuitry 455 filters and amplifies the amplitude (RSSI) signal from receiver 442. This signal is sent to an A/D channel of the microcomputer via strength signal line 457 to determine the signal strength. This signal strength is then used by the microcomputer to control which antenna to select for receiving communication from the implanted device 12.

The telemetry transmitter is implemented using the direct digital synthesizer (DDS) 461 of transmit signal generator 460. The DDS has two frequency registers allowing for operation at two frequencies selected by a digital line 462 from the UART of the microcomputer for providing FSK modulation. The DDS 461 output 463 is provided to transmit output amplifier circuitry 470 for amplification by operational amplifier 471.

Analog switch 472 of the transmit output amplifier circuitry 470 controls the signal to the operational amplifier 471. Analog switches 411–413 of the analog switch/driver circuitry 410 control the signal provided from the operational amplifier 471 to the push-pull transistor outputs 415–417 used to drive the antennas 302, 304, 306, respectively. The antenna being used for transmission must be enabled by the receiver analog switches 421–423 of analog selection circuitry 420 to remove the short circuit from the antenna being used. As such control of the antenna used for transmission is determined based on the strength of the signal received from the three antennas and provided to the microcomputer via the strength indication circuitry 455. The microcomputer controls selection of the transmit/receive mode. This selection includes selection of the UART direction via the data logic control device described above, enabling of the transmitter analog switch 472, and the transmitter drive switches 411–413.

The antennas 302, 304, 306 are tuned with the variable capacitors, 303, 305, 307, respectively, to be resonant at 2.7 MHz. If needed, these capacitors can be paralleled with fixed capacitors, 311, 312, 313, respectively, to reach resonance if the value of the variable capacitor is not large enough.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the body as an antenna for an implanted device. Various modifications of the illustrative embodiments, as well as additional embodiments of the invention, will be apparent to persons skilled in the art upon reference to this description.

In the claims, means plus function clauses are intended to cover the structures described herein as performing the recited function and not only structural equivalents but also equivalent structures. Thus, for example, although a nail and a screw may not be structural equivalents in that a nail employs a cylindrical surface to secure wood parts together, whereas a screw employs a helical surface, in the environment of fastening wooden parts, a nail and a screw are equivalent structures.

What is claimed is:

1. An implantable medical device telemetry method, the method comprising the steps of:

providing an implanted device in a body, the implanted device including a housing having a transmitter positioned therein, and a body antenna that optimally adapts the body for use as an antenna;

providing communication device external to the body, the external communication device including at least a receiver connected to an antenna;

providing an output signal generated by the transmitter into the body via the body antenna external to the housing of the implanted device, wherein the output signal is modulated to include data, and further wherein the modulated output signal is propagated by the body to radiate electromagnetic waves representative of the modulated output signal in a near-field communication volume surrounding the body; and receiving the radiated electromagnetic waves at the antenna of the external communication device when the antenna is positioned within the near-field communication volume and recovering the data therefrom by the receiver of the external communication device.

2. The method of claim 1, wherein the step of providing the output signal into the body includes the step of providing a modulated output current external of the housing of the implanted device to generate an asymmetrical current distribution within the body.

3. The method of claim 2, wherein the step of providing the output signal into the body includes the step of injecting output current into the body from a lead extending from the body antenna with the housing providing a return path for the output current.

4. The method of claim 3, wherein the step of injecting the output signal into the body from the lead includes the step of injecting the output current into the body from a therapeutic lead.

5. The method of claim 1, wherein the step of providing the output signal into the body includes the step of providing the output signal into the body via a matching network, wherein the matching network is used to match the impedance of the body to characteristics of the body antenna.

6. The method of claim 5, wherein the step of providing the output signal into the body includes the step of forming a resonant circuit having a quality factor (Q), wherein the resonant circuit is formed of the matching network and the body.

7. The method of claim 6, wherein the step of forming a resonant circuit having a quality factor (Q) includes forming a resonant circuit having a Q in the range of about 5 to about 15.

8. The method of claim 1, wherein the step of providing the output signal generated by the transmitter includes driving the output of the transmitter using a battery drive current in the range of about 5 microamperes to about 50 microamperes.

9. The method of claim 1, wherein the step of providing an implanted device in the body includes the step of providing an implanted device that further includes a receiver and wherein the step of providing a communication device external to the body includes the step of providing a communication device that further includes a transmitter, and further wherein the method includes the steps of:

radiating electromagnetic waves from the antenna of the external communication device within the near-field communication volume, wherein the electromagnetic waves are representative of output signals generated by the transmitter of the external communication device modulated to include data, and further wherein the body converts the electromagnetic waves into electrical signals propagated in the body; and filtering the electrical signals at the receiver of the implanted device to recover the data from the electrical signals.

10. The method of claim 9, wherein the step of filtering of the electrical signals includes the step of providing a matching network for matching the impedance of the body and forming a resonant circuit with the body, wherein the resonant circuit provides a bandpass filter for recovery of the data from the electrical signals.

11. The method of claim 1, wherein the step of receiving the radiated electromagnetic waves at the antenna of the external communication device includes the steps of:

establishing a communication link between the transmitter of the implanted device and the external communication device when the antenna of the external communication device is at a first position within the near-field communication volume; and moving the antenna of the external communication device to other positions anywhere within the near-field communication volume surrounding the body without loss of the communication link.

12. The method of claim 1, wherein the step of providing an implanted device includes the step of providing an implanted device selected from one of a pacemaker, a defibrillator, a pacemaker/cardioverter/defibrillator, a cardiovertor/defibrillator, a brain stimulator, a neurostimulator, a muscle stimulator, a gastric stimulator, an implantable monitor, a hemodynamic monitor, and a drug pump.

13. An implantable medical device telemetry method, the method comprising the steps of:

providing an implanted device in a body, the implanted device including a housing having at least one of a transmitter and a receiver positioned within the housing;

providing a communication device external to the body, the external communication device including at least one of a receiver and a transmitter connected to an antenna; and electrically coupling at least one of the transmitter and receiver of the implanted device to the body such that the body functions as an antenna for at least one of the transmitter and receiver of the implanted device to facilitate communication of data between the implanted device and the external communication device.

14. The method of claim 13, wherein the step of electrically coupling at least one of the transmitter and receiver of the implanted device to the body includes the step of providing an output signal generated by the transmitter into the body external of the housing of the implanted device, wherein the output signal is modulated to include data, and further wherein the modulated output signal is propagated in the body such that the body functions as the antenna to radiate electromagnetic waves representative of the modulated output signal in a near-field communication volume surrounding the body.

15. The method of claim 14, wherein the step of providing the modulated output signal into the body includes the step of providing a modulated output current external of the housing of the implanted device to generate an asymmetrical current distribution within the body.

16. The method of claim 15, wherein the step of providing the modulated output current into the body includes the step of injecting the modulated output current into the body from a lead extending from a position external of the housing with the housing as a return path for the modulated output current.

17. The method of claim 14 wherein the step of providing the output signal generated by the transmitter includes driving the output of the transmitter using a battery drive current in the range of about 5 microamperes to about 50 microamperes.

18. The method of claim 13, wherein the step of electrically coupling at least one of the transmitter and receiver of the implanted device to the body includes the step of providing a matching network to match the impedance of the body.

19. The method of claim 18, wherein the step of providing a matching network includes the step of forming a resonant circuit having a quality factor (Q), wherein the resonant circuit is formed by the matching network and the body.

20. The method of claim 19, wherein the step of forming a resonant circuit having a quality factor (Q) includes the step of forming a resonant circuit having a Q in the range of about 5 to about 15.

21. The method of claim 13, wherein the step of electrically coupling at least one of the transmitter and receiver of the implanted device to the body includes the steps of:

radiating electromagnetic waves from the antenna of the external communication device within a near-field communication volume surrounding the body, wherein the electromagnetic waves are representative of output signals generated by the transmitter of the external communication device modulated to include data, and further wherein the body converts the electromagnetic waves into electrical signals propagated in the body; and filtering the electrical signals at the receiver of the implanted device to recover the data from the electrical signals.

22. The method of claim 21, wherein the step of filtering the electrical signals includes the step of providing a matching network for matching the impedance of the body and forming a resonant circuit with the body, wherein the resonant circuit provides a bandpass filter for use in recovery of the data from the electrical signals.

23. The method of claim 13, wherein the step of electrically coupling at least one of the transmitter and receiver of the implanted device to the body includes the steps of:
 establishing a communication link between the implanted device and the external communication device when the antenna is at a first position within the near-field communication volume; and
 moving the antenna of the external communication device to other positions anywhere within the communication volume without loss of the communication link.

24. The method of claim 13, wherein the implanted device is selected from one of a pacemaker, a defibrillator, a neurostimulator, a pacemaker/cardiovertor/defibrillator, a cardiovertor/defibrillator, a brain stimulator, a muscle stimulator, a gastric stimulator, an implantable monitor, a hemodynamic monitor, and a drug pump.

25. An implantable medical device for implantation within a body, the device comprising:
 a housing;
 at least one of a transmitter and receiver positioned within the housing operable for providing a modulated output signal or for receiving a modulated signal, respectively;
 a conductive element extending from an interior of the housing to a position external of the housing; and
 a matching network electrically coupling at least one of the transmitter and receiver to the conductive element, wherein the matching network is selected to match the impedance of the body.

26. The device of claim 25, wherein the matching network and the body when the implantable device is implanted therein form a resonant circuit having a quality factor (Q).

27. The device of claim 26, wherein Q is in the range of about 5 to about 15.

28. The device of claim 26, wherein the resonant circuit provides a bandpass filter for providing filtered signals to the receiver.

29. The device of claim 25, wherein the matching network includes a transformer.

30. The device of claim 25, wherein the matching network includes inductive and capacitive elements.

31. The device of claim 25, wherein the modulated output signal is an output current from the transmitter driven by a battery drive current in the range of about 5 microamperes to about 50 microamperes.

32. The method of claim 25, wherein conductive element is a therapeutic lead extending from the interior of the housing.

33. The method of claim 25, wherein the implanted device is selected from one of a pacemaker, a defibrillator, a neurostimulator, a pacemaker/cardiovertor/defibrillator, a cardiovertor/defibrillator, a brain stimulator, a muscle stimulator, a gastric stimulator, an implantable monitor, a hemodynamic monitor and a drug pump.

34. An implantable medical device telemetry system, the system comprising:
 an external communication device, the external communication device including at least one of a receiver and a transmitter connected to an antenna; and
 an implantable medical device, the implantable medical device including a housing having at least one of a transmitter and a receiver positioned within the housing, the implantable device further including a coupling network for electrically coupling at least one of the transmitter and receiver of the implanted device to the body such that the body functions as an antenna for at least one of the transmitter and receiver of the implanted device to facilitate communication of data between the implanted device and the external communication device.

35. The system of claim 34, wherein the antenna of the external communication device is a three orthogonal axis antenna configuration.

36. The system of claim 35, wherein the external communication device includes:
 means for monitoring signals received by three orthogonal axis elements; and
 means for selecting one or more of the three orthogonal axis elements to facilitate communication of data between the implanted device and the external communication device based on the monitored signals.

37. The system of claim 34, wherein the implanted device is selected from one of a pacemaker, a defibrillator, a neurostimulator, a pacemaker/cardiovertor/defibrillator, a cardiovertor/defibrillator, a brain stimulator, a muscle stimulator, a gastric stimulator, an implantable monitor, a hemodynamic monitor and a drug pump.

38. The system of claim 34, wherein the coupling network includes a matching network electrically coupling at least one of the transmitter and receiver to a conductive element extending from the interior of the housing to a position external to the housing, wherein the matching network is selected to match the impedance of the body.

39. The system of claim 38, wherein the matching network and the body when the implantable device is implanted therein form a resonant circuit having a quality factor (Q).

40. The system of claim 39, wherein the resonant circuit provides a bandpass filter for providing filtered signals to the receiver of the implanted medical device.

41. The system of claim 38, wherein conductive element is a therapeutic lead extending from the interior of the housing.

42. An implantable medical device transmission method, the method comprising the steps of:
 providing an implanted device in a body, the implanted device including a housing having at least a transmitter positioned within the housing; and
 generating electromagnetic waves in a communication volume surrounding the body, wherein the step of generating the electromagnetic waves includes the step of using the body as an antenna for the transmitter of the implanted device.

43. The method of claim 42, wherein the step of generating electromagnetic waves in the communication volume includes the step of providing an output signal generated by the transmitter into the body external of the housing of the implanted device, wherein the output signal is modulated to include data, and further wherein the step of generating electromagnetic waves in the communication volume includes the step of propagating the output signal in the body to radiate electromagnetic waves representative of the modulated output signal in the communication volume.

44. The method of claim 43, wherein the step of providing the output signal into the body includes the step of providing a modulated output current external of the housing of the implanted device to generate an asymmetrical current distribution within the body.

45. The method of claim 44, wherein the step of providing the output signal into the body includes the step of injecting the output current into the body from a lead extending from a position within the housing to a position external to the housing with the housing as a return path for the output current.

46. The method of claim 45, wherein the step of injecting the output signal into the body from a lead includes the step of injecting the output current into the body from a therapeutic lead.

47. The method of claim 43, wherein the step of providing the output signal into the body includes the step of providing the output signal into the body via a matching network, wherein the matching network is used to match the impedance of the body.

48. The method of claim 47, wherein the step of providing the output signal into the body includes the step of forming a resonant circuit having a quality factor (Q), wherein the resonant circuit is formed of the matching network and the body.

49. The method of claim 48, wherein the step of forming a resonant circuit having a quality factor (Q) includes forming a resonant circuit having a Q in the range of about 5 to about 15.

50. The method of claim 43, wherein the step of providing the output signal generated by the transmitter includes driving the output of the transmitter using a battery drive current in the range of about 5 microamperes to about 50 microamperes.

51. The method of claim 42, wherein the step of providing an implanted device includes the step of providing an implanted device selected from one of a pacemaker, a defibrillator, a pacemaker/cardioverter/defibrillator, a cardiovertor/defibrillator, a brain stimulator, a neurostimulator, a muscle stimulator, a gastric stimulator, an implantable monitor, a hemodynamic monitor, and a drug pump.

52. An implantable medical device for implantation within a body, the device comprising:

a housing;

transmission means positioned within the housing operable for providing a modulated output signal; and means for coupling the output signal into the body such that electromagnetic waves representative of the modulated output signal are transmitted into a communication volume surrounding the body when the implantable medical device is operable within the body.

53. The device of claim 52, wherein the means for coupling includes means for matching the impedance of the body.

54. The device of claim 53, wherein the means for matching the impedance of the body and the impedance of the body form a resonant circuit having a quality factor (Q).

55. The device of claim 54, wherein Q is in the range of about 5 to about 15.

56. The device of claim 54, wherein device further includes a receiver positioned within the housing, and further the resonant circuit provides a bandpass filter for providing filtered signals to the receiver.

57. The device of claim 52, wherein the means for coupling includes a transformer.

58. The device of claim 52, wherein the means for coupling includes inductive and capacitive elements.

59. The device of claim 52, wherein the modulated output signal is an output current from the transmitter driven by a battery drive current in the range of about 5 microamperes to about 50 microamperes.

60. The device of claim 52, wherein means for coupling includes a conductive element extending from the interior of the housing.

61. The device of claim 60, wherein the conductive element is a therapeutic lead extending from the interior of the housing.

62. The device of claim 52, wherein the implanted device is selected from one of a pacemaker, a defibrillator, a neurostimulator, a pacemaker/cardioverter/defibrillator, a cardioverter/defibrillator, a brain stimulator, a muscle stimulator, a gastric stimulator, an implantable monitor, a hemodynamic monitor and a drug pump.

63. An implantable medical device telemetry system comprising:

a communication device external to a body; and an implantable device for implant in the body, the implantable device including a housing with a transmitter and a receiver positioned within the housing for facilitating communication with the external communication device using the body as an antenna for the transmitter and the receiver.

64. The system of claim 63, wherein the external communication device includes at least one of a receiver and a transmitter connected to an antenna, and further wherein the antenna of the external communication device is a three orthogonal axis antenna configuration.

65. The system of claim 64, wherein the external communication device further includes:

means for monitoring signals received by each of three orthogonal axis elements of the antenna configuration; and means for selecting one or more of the three orthogonal axis elements to facilitate communication of data between the implanted device and the external communication device based on the monitored signals.

* * * * *

UNITED STATES PATENT AND TRADEMARK OFFICE
CERTIFICATE OF CORRECTION

PATENT NO. : 6,115,636

DATED : SEPTEMBER 5, 2000

INVENTOR(S) : RYAN

It is certified that error appears in the above-identified patent and that said Letters Patent is hereby corrected as shown below:

Col. 20, line 42, claim 1: "providing communication" should read --providing a communication--

Signed and Sealed this

First Day of May, 2001

Attest:

NICHOLAS P. GODICI

*Attesting Officer*     *Acting Director of the United States Patent and Trademark Office*